(12) United States Patent
Zagotto et al.

(10) Patent No.: US 11,345,673 B2
(45) Date of Patent: May 31, 2022

(54) 1-PHENYLPROPANONE COMPOUNDS AND USE THEREOF

(71) Applicant: UNIVERSITA' DEGLI STUDI DI PADOVA, Padua (IT)

(72) Inventors: Giuseppe Zagotto, Roncà (IT); Giovanni Ribaudo, Padua (IT); Anna Maria Brunati, San Martino di Lupari (IT); Mario Angelo Primo Pagano, Padua (IT); Elena Tibaldi, Verona (IT); Livio Trentin, Susegana (IT)

(73) Assignee: UNIVERSITÀ DEGLI STUDI DI PADOVA

( * ) Notice: Subject to any disclaimer, the term of this patent is extended or adjusted under 35 U.S.C. 154(b) by 0 days.

(21) Appl. No.: 16/338,607

(22) PCT Filed: Sep. 29, 2017

(86) PCT No.: PCT/IB2017/056010
§ 371 (c)(1),
(2) Date: Apr. 1, 2019

(87) PCT Pub. No.: WO2018/060947
PCT Pub. Date: Apr. 5, 2018

(65) Prior Publication Data
US 2020/0039946 A1 Feb. 6, 2020

(30) Foreign Application Priority Data
Sep. 30, 2016 (IT) .................. 102016000098338

(51) Int. Cl.
| | |
|---|---|
| *A61K 31/5375* | (2006.01) |
| *A61K 31/495* | (2006.01) |
| *A61K 31/4453* | (2006.01) |
| *C07D 295/108* | (2006.01) |
| *C07D 211/14* | (2006.01) |
| *C07D 211/06* | (2006.01) |
| *C07D 241/04* | (2006.01) |
| *A61P 35/00* | (2006.01) |
| *C07F 11/00* | (2006.01) |

(52) U.S. Cl.
CPC .......... *C07D 295/108* (2013.01); *A61P 35/00* (2018.01); *C07D 211/06* (2013.01); *C07D 241/04* (2013.01); *C07F 11/00* (2013.01)

(58) Field of Classification Search
CPC .............. A61K 31/5375; A61K 31/495; A61K 31/4453; C07D 295/108; C07D 211/14; C07D 211/06; C07D 241/04; A61P 35/00
USPC ...... 514/239.5, 238.8, 252.13, 317; 544/175, 544/403, 399; 546/237
See application file for complete search history.

(56) References Cited

U.S. PATENT DOCUMENTS

2011/0136888 A1  6/2011  Delhomel et al.
2012/0136063 A1  5/2012  Chen et al.

FOREIGN PATENT DOCUMENTS

| DE | 2842091 A1 | 4/1980 | |
|---|---|---|---|
| FR | 2902789 A1 | 12/2007 | |
| WO | 200128550 A1 | 4/2001 | |
| WO | 2007143081 A2 | 12/2007 | |
| WO | WO-2009045443 A2 * | 4/2009 | ........... G01N 33/574 |

OTHER PUBLICATIONS

STN CAS Registry No. 1527849-11-1 (Entered STN: Jan. 23, 2014) (Year: 2014).*
STN CAS Registry No. 732181-05-4 (Entered STN: Aug. 24, 2004) (Year: 2004).*
Leggy et al., "Inhibitors of the Interaction of a Thyroid Hormone Receptor and Coactivators: Preliminary Structure-Activity Relationships," Journal of Medicinal Chemistry 50(22):5269-5280 (2007).
Donghong et al., "Dyclonine Enhances the Cytotoxic Effect of Proteasome Inhibitor Bortezomib in Multiple Myeloma Cells," Molecular Medicine Reports 10:2609-2612 (2014).
Donghong et al., "Dyclonine and Alverine Citrate Enhance the Cytotoxic Effects of Proteasome Inhibitor MG123 on Breast Cancer Cells," International Journal of Molecular Medicine 23:205-209 (2009).
STN Database Accession No. 1971:97721.
STN Database Accession No. 1964:34916.
STN Database Accession No. 1962:48327.
PCT International Search Report and Written Opinion for corresponding PCT/IB2017/056010, dated Dec. 22, 2017.

* cited by examiner

*Primary Examiner* — Joseph R Kosack
*Assistant Examiner* — Sagar Patel
(74) *Attorney, Agent, or Firm* — Troutman Pepper Hamilton Sanders LLP (Rochester)

(57) ABSTRACT

The present invention relates to a 1-phenylpropanone compound of formula (I), wherein X is $CH_2$ or an atom selected from the group consisting of O, S and Se, n is an integer from 4 to 6, A is a substituent selected from the group consisting of 4-morpholyl, 1-piperidinyl, 4-methyl-1-piperazinyl, A being optionally substituted with a $(C_1-C_3)$alkyl or $(C_1-C_3)$acyl substituent, with the proviso that when X is $CH_2$, n is equal to 5, for use as an antitumoral agent in the treatment of breast cancer, chronic lymphatic leukemia or neuroblastoma. The invention also concerns new 1-phenylpropanone compounds, and compounds as antitumoral agents.

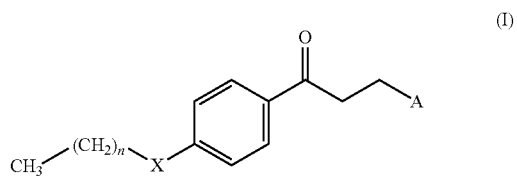

(I)

26 Claims, 1 Drawing Sheet

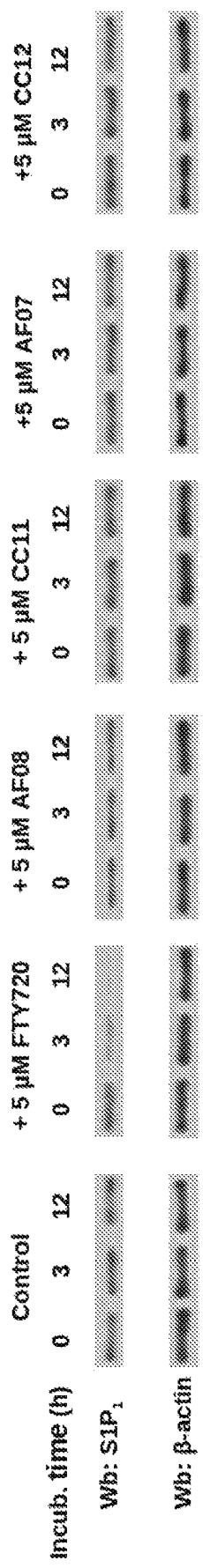

1-PHENYLPROPANONE COMPOUNDS AND USE THEREOF

This application is a national stage application under 35 U.S.C. § 371 of PCT International Application Serial No. PCT/IB2017/056010, filed Sep. 29, 2017, which claims priority benefit of Italy Application No. 102016000098338, filed Sep. 30, 2016, which are hereby incorporated by reference in their entirety.

FIELD OF THE INVENTION

The present invention concerns 1-phenylpropanone compounds effective in the induction of apoptosis in malignant B cells of patients affected by chronic lymphocytic leukemia and other cellular models of several tumor types in vitro.

STATE OF THE ART

FTY720 (also known as fingolimod, and marketed by Novartis as Gilenya™), i.e. 2-amino-2[2-(4-octylphenyl)ethyl]propane-1,3-diol hydrochloride, having the formula reported below

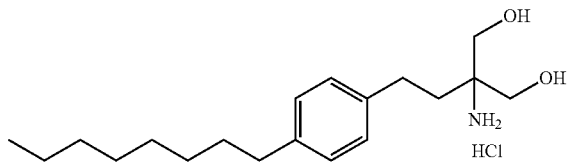 [SMILES: CCCCCCCCc1ccc(CCC(N)(CO)CO)cc1 ; Cl]

is a structural analogue of sphingosine, synthesized by modification of the natural compound, with immunosuppressive action, known as miriocine, alias ISP-I, a metabolite of the entomopathogenic fungus *Isaria sinclairii*, (Fujita T et al, J Antibiot., 1994, 47:208-15). The latter, having a powerful immunosuppressive activity, has been used as lead compound to develop more effective immunosuppressants with lesser side effects [Adachi et al., Bioorg. Med. Chem. Lett. 1995; 5:853-56; Adachi K., Chiba K., Perspect Medicin Chem 2008; 1:11-23.2]. FTY720 was initially tested as a potential drug in the prevention of post-transplant rejection, as such or in combination with classical immunosuppressants, such as cyclosporin [Chiba K. et al., Transplant Proc. 1996, 28(2):1056-1059; Brinkmann et al, J Biol Chem. 2002, 277(24):21453-21457], but showed no superiority over cyclosporine in this field, pointing the interest towards the inhibition effect on the lymphocytes migration into secondary lymphoid organs, thus opening up new potential opportunities in the treatment of immune disorders, such as multiple sclerosis [Mansoor M., Melendez A. J., Rev Recent Clin Trials. 2008, 3(1):62-69]. FTY720 was approved for the treatment of the latter, in particular the relapsing-remitting form, in 2010 and 2011, by FDA in USA and by the European Medicines Agency in Europe, respectively.

The immunosuppressive activity of FTY720 is related to its transformation into the phosphorylated form (FTY720-P) in lymphocytes by the enzyme sphingosine kinase 2 (SphK2), which recognizes the drug because it is structurally similar to the natural substrate, sphingosine. Subsequently, FTY720-P is extruded from the cell, and it interacts with the G-protein coupled sphingosine-1-phosphate (S1P) receptors (especially the one called S1P1), causing their internalization and degradation. In the absence of these receptors, lymphosphingocyte, being no longer able to interact with the natural ligand S1P, are sequestered in secondary lymphoid organs, resulting in lymphopenia in the general circulation [Brinkmann et al. Nat Rev Drug Discov. 2010 November, 9(11):883-9; and patent application WO 2007/143081 A2]. During studies aimed to explore FTY720 induced lymphopenia, it was observed that this agent induced apoptosis in peripheral lymphocytes [Nagahara et al., Immunopharmacology 2000, 48:75-85; Nagahara et al., J Immunol 2000, 165:3250-3259; Fufino M., Li X. K., Kitazawa Y. et al., J Pharmacol Exp Thar 2002, 300:939-45], and this led to assessment of its potential as antitumoral agent [Pinschewer D. D., Brinkmann V., Mender D., Neurology 2011, 76:515-9]. It was thus demonstrated that FTY720 is able to induce apoptosis in cells derived from both hematological [Liu et al., Blood 2008, 111:275-84; Neviani et al., J Cin Invest 2007, 117: 2408-21], and solid neoplasm, such as prostate, bladder, kidney, pancreas, liver, breast, colon, stomach, and lungs [Permpongkosol et al. Int J Cancer 2002, 98:167sfingo-72; Azuma et al., J Urol 2003, 169:2372-7; Ubel et al., Anticancer Res 2007, 27:75-88; Shen et al., Cancer Lett 2007, 254:288-97; Ho et al., Mol Cancer Thor 2005, 4:1430-8; Azuma et al., Cancer Res 2002, 62:1410-9; Nagaoka et al., Bid Pharm 2008, 31:117741; Meng et al., J Cell Biochem 2010, 111:218-28; Salinas et al. Int Immunopharmacol 2009, 9:689-93]. With regard to the molecular mechanism underlying cell death, caspase-dependent apoptotic pathways have been called into question, with the involvement of caspases 9 and 3 [Zheng et al., sfingo J Cell Biochem 111:218-228, 2010], sometimes associated with the increase in the expression of the pro-apoptotic proteins Bad, Bax, Bid, and Btf [Ubai et al., Anticancer Res 27:75-88, 2007], and caspase-independent, in which a role is played by the activation state of protein kinases, such as Akt [Liu et al., Clin Cancer Res 16:3182-3192, 2010] and ERK1/2 [Liu et al., Blood 111:275-284; 200824], the generation of oxygen reactive species [Wallington-Beddoe et al., Autophagy 7:707-715, 2011], and autophagy induction [Liu et al., Clin Cancer Res 16:3182-3192, 2010; Liu et al., Blood 111:275-284, 2008], as well as autophagy [Zhang N. et al., Autophagy 6:1157-1167, 2010; Wallington-Beddoe et al., Autophagy 7:707-715, 2011; Liao et al., Eur J Pharm Sci 45:600-605, 2012], depending on the cell type. It is to be noted that the ability of FTY720 to induce cell death in tumor cells is independent of drug phosphorylation, and thus of immunosuppression mechanisms [Wallington-Beddoe et al., Autophagy 7:707-715, 2011]. Despite the fact that the mechanisms mediating cell death by FTY720 have not yet been fully clarified, molecular targets of the non-phosphorylated form of FTY720 have been proposed to explain this biological effect. While on one hand, the generation of reactive oxygen species in the induction of cell death by FTY720 in acute lymphoblastic leukemia [Wallington-Beddoe et al., Autophagy 7:707-715, 2011], mantle lymphoma [Liu et al., Clin Cancer Res 16:3182-3192, 2010] and multiple myeloma [Liao et al., Eur J Pharm Sci 45:600-605, 2012] was called into question, on the other hand this compound may adversely regulate the activity of critical protein factors of signal transduction pathways involved in the genesis and maintenance of the tumor phenotype, resulting in its activation, such as Protein Phosphatase 2A [Neviani et al., Cancer Cell 8:355-368, 2005; Neviani et al., J Clin Invest 117:2408-2421, 2007], the so-called MAPKs (Mitogen-activated protein kinase) pathway [Ubai et al., Anticancer Res 27:75-88, 2007; Estrada-Bernal et al., Neuro Oncol 14:405-415, 2012], the PI3K/AKT cascade [Zheng et al., J Cell Biochem 111:218-228, 2010; Liu et al., Clin Cancer Res 16:3182-3192, 2010] and the 14-3-3 adaptive protein [Woodcock et al., Cell Signal 22:1291-1299, 2010], to name just a few.

Although these observations indicate an antitumoral effect in pre-clinical models, thus allowing them to undergo further investigations to evaluate their use in human therapy, its contraindications since its approval into the market include indeed neoplasms in active phase, as well as immunodeficiencies, including the secondary ones that could be induced by chemotherapy agents.

In addition, immunosuppression, although indicated, for example, for the treatment of immunologically mediated diseases or the prevention of rejection, may increase susceptibility of the host to infections or even tumors; immunosuppression should therefore always be taken into account and, as far as possible, minimized.

Molecules with structure analogous to FTY720 have already been described in the literature.

In the article "Inhibitors of the interaction of thyroid hormone receptor and coactivators: preliminary structure-activity relationships", L. A. Arnold et al., J Med Chem. 2007 Nov. 1; 50(22): 5269-5280, 1-phenylpropanone derivatives exhibiting cytotoxic activity, although mainly against ARO cell lines (anaplastic thyroid cancer cells), are disclosed.

The articles "Dyclonine and alverine citrate enhance the cytotoxic effects of proteasome inhibitor MG132 on breast cancer cells", D. Ju et al., Int J Mol Med. 2009 February, 23(2):205-9, and "Dyclonine enhances the cytotoxic effect of proteasome inhibitor bortezomib in multiple myeloma cells", D. Ju et al., MOLECULAR MEDICINE REPORTS 10: 2609-2612, 2014, report the properties of dyclonine molecule, having the formula below, as adjuvant in the treatment of cancer:

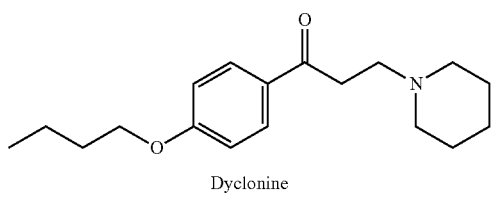 [SMILES: CCCCOc1ccc(C(=O)CCN2CCCCC2)cc1]

Dyclonine

Specifically, in the first of the two cited articles, the activity of dyclonine in breast cancer is investigated, while in the second the activity against multiple myeloma is investigated. In both cases, in vitro studies conclude that dyclonine is able to significantly increase the cytotoxic efficacy of MG132 protease inhibitor (known in the treatment of breast cancer) and of drug bortezomib (known for the treatment of multiple myeloma) against target cells, but alone it has very limited cytotoxic effects.

It is therefore an object of the invention to provide alternative solutions through the design of molecules that exhibit a proapoptotic action against tumor cells, with high potency and at the same time without immunosuppressive properties.

SUMMARY OF THE INVENTION

The above object is achieved by the synthesis and study of 1-phenylpropanone compounds of the general formula (I)

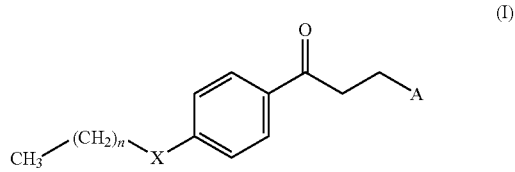

which have been shown to induce cell death by apoptosis in cellular models of neoplasia in vitro, and in the absence of an immunosuppressive action, wherein:

X is a methylene group ($-CH_2-$) or an atom selected from the group consisting of O, S and Se, n is an integer from 4 to 6, A is a substituent selected from the group consisting of 4-morpholyl, 1-piperidinyl and 4-methyl-1-piperazinyl, and it is optionally substituted with a ($C_1$-$C_3$)alkyl or ($C_1$-$C_3$) acyl radical, with the proviso that when X is $CH_2$, n is equal to 5, for use as an antitumoral agent in the treatment of breast cancer, chronic lymphatic leukemia (LLC) or neuroblastoma.

The inventors have also synthesized new 1-phenylpropanone derivative compounds that resulted to have apoptotic activity against tumor cells.

In another aspect, the invention therefore concerns a compound of formula (I)

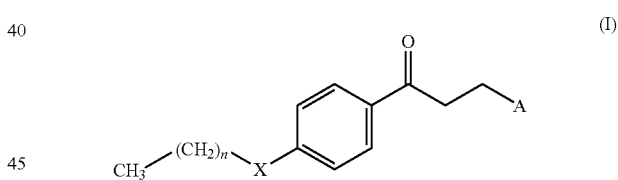

wherein:

X is a methylene group ($-CH_2-$) or an atom selected from the group consisting of O, S and Se, n is an integer from 4 to 6, A is a substituent selected from the group consisting of 4-morpholyl, 1-piperidinyl and 4-methyl-1-piperazinyl, and it is optionally substituted with a ($C_1$-$C_3$)alkyl or ($C_1$-$C_3$) acyl radical, with the proviso that when X is O, A is 4-methyl-1-piperazinyl, and n is equal to 6, when X is S and n is 5, then A is 4-methyl-1-piperazinyl, when X is Se and A is 1-piperidinyl, then n is 6, when X is $CH_2$, n is equal to 5, and A is 4-methyl-1-piperazinyl or 4-morpholyl.

In a further aspect the invention concerns a compound of formula (I)

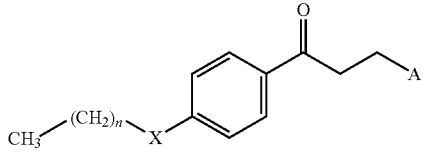

wherein:
X is a methylene group (—CH$_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a (C$_1$-C$_3$)alkyl or (C$_1$-C$_3$) acyl radical,
with the proviso that
when X is O, A is 4-methyl-1-piperazinyl, and n is equal to 6,
when X is S and n is 5, then A is 4-methyl-1-piperazinyl o 4-morpholyl,
when X is Se and A is 1-piperidinyl, then n is 6,
when X is CH$_2$, n is equal to 5, and A is 4-methyl-1-piperazinyl or 4-morpholyl for use as a medicament.

In a further aspect the invention relates to a pharmaceutical composition comprising a compound of formula (I) as a medicament, and a pharmaceutically acceptable vehicle thereof.

In yet a further aspect, the invention concerns a compound of formula (I)

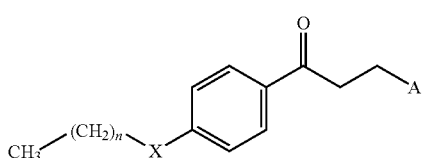

wherein:
X is a methylene group (—CH$_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a (C$_1$-C$_3$)alkyl or (C$_1$-C$_3$) acyl radical,
with the proviso that
when X is O, A is 4-methyl-1-piperazinyl or 1-piperidinyl, and n is equal to 6,
when X is CH$_2$, n is 5 for use as an antitumoral agent.

Preferably, the antitumoral treatment is against breast cancer, hepatocarcinoma, chronic lymphatic leukemia (LLC) or neuroblastoma.

BRIEF DESCRIPTION OF THE FIGURES

FIG. 1 shows the results of tests aimed at assessing the immunosuppression characteristics of compounds of the invention and, by comparison, of a compound of the prior art.

DETAILED DESCRIPTION OF THE INVENTION

In the compounds of the invention, the optional substituent C$_3$-alkyl of substituent A may be either n-propyl or isopropyl.

The invention relates to a 1-phenylpropanone compound of formula (I)

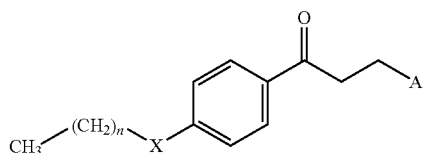

wherein
X is a methylene group (—CH$_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a (C$_1$-C$_3$)alkyl or (C$_1$-C$_3$) acyl radical,
with the proviso that when X is CH$_2$, n is equal to 5,
for use as an antitumoral agent in the treatment of breast cancer, chronic lymphatic leukemia (LLC) or neuroblastoma.

In the treatment of breast cancer, chronic lymphatic leukemia (LLC) or neuroblastoma, the compound of the invention is preferably
a compound wherein X is S, Se or CH$_2$, more preferably S;
a compound wherein n is 5 or 6.
A is optionally substituted with a (C$_1$-C$_3$)alkyl or (C$_1$-C$_3$) acyl substituent.

Preferably, in the treatment of breast cancer, chronic lymphatic leukemia (LLC) or neuroblastoma, the compound of formula (I) is selected from the group consisting of:

Compound 1 (AF08)

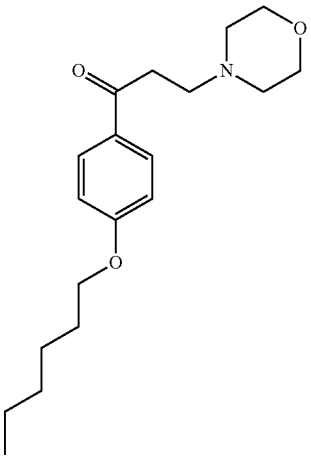

1-(4-(hexyloxy)phenyl)-3-morpholinopropan-1-one,

Compound 2 (CC11)
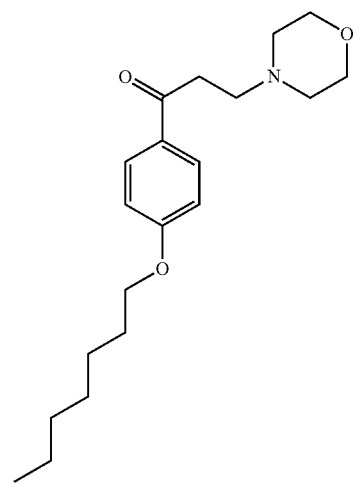
1-(4-(heptyloxy)phenyl)-3-morpholinopropan-1-one
Compound 3 (AF07)
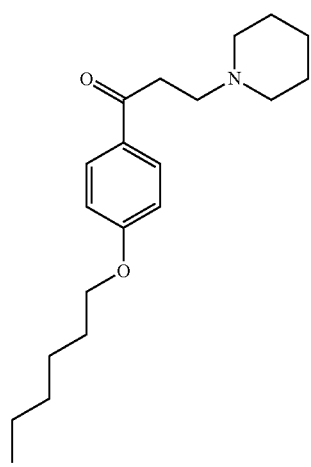
1-(4-(hexyloxy)phenyl)-3-(piperidin-1-yl)propan-1-one,
Compound 4 (CC12)
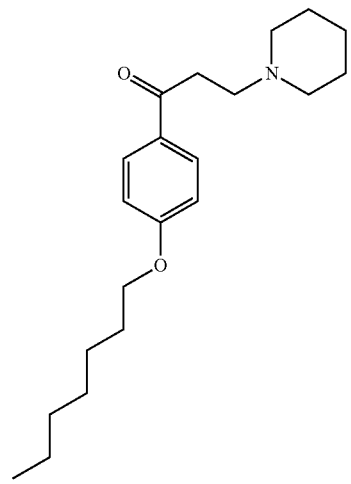
1-(4-(heptyloxy)phenyl)-3-(piperidin-1-yl)propan-1-one,
Compound 5 (AI01)
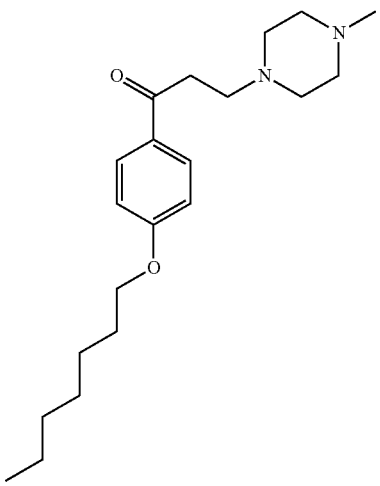
1-(4-(heptyloxy)phenyl)-3-(4-methylpiperazin-1-yl)propan-1-one,
Compound 6 (MD63)
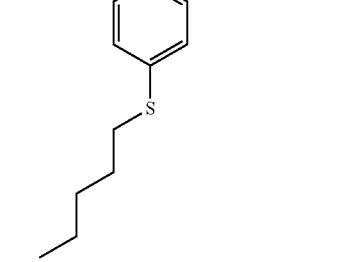
3-morpholino-1-(4-(pentylthio)phenyl)propan-1-one,
Compound 7 (VP158)
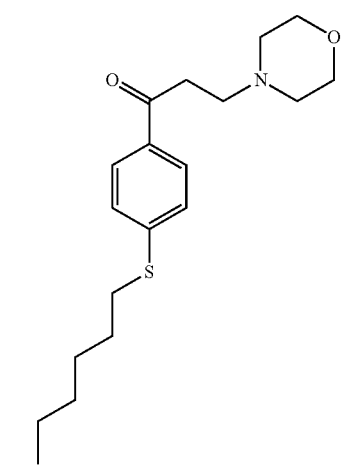
1-(4-(hexylthio)phenyl)-3-morpholinopropan-1-one, Compound 8 (FT017)
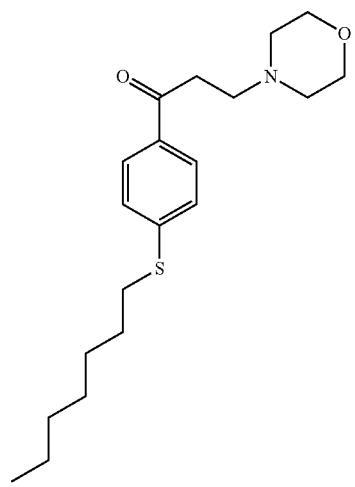
1-(4-(heptylthio)phenyl)-3-morpholinopropan-1-one,
Compound 9 (MC12)
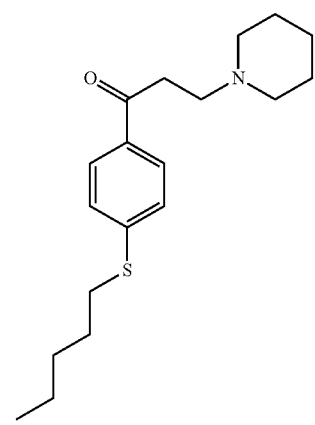
1-(4-(pentylthio)phenyl-3-(piperidin-1-yl)propan-1-one,
Compound 10 (VP157)
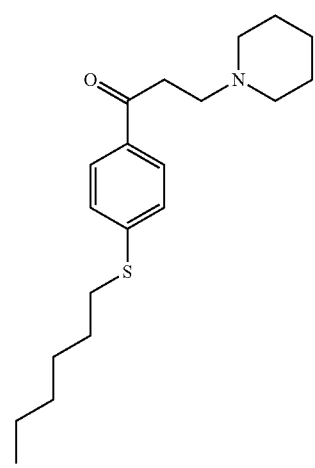
1-(4-(hexylthio)phenyl)-3-(piperidin-1-yl)propan-1-one,
Compound 11 (FT018)
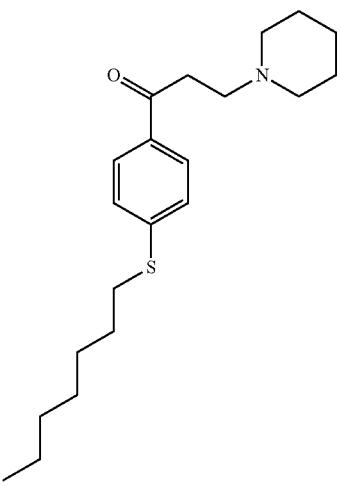
1-(4-(heptylthio)phenyl)-3-(piperidin-1-yl)propan-1-one,
Compound 12 (FT013)
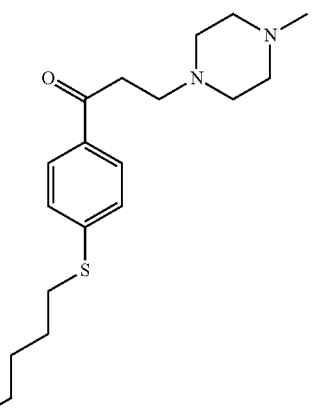
3-(4-methylpiperazin-1-yl)-1-(4-pentylthio)phenyl)propan-1-one,
Compound 13 (FT016)
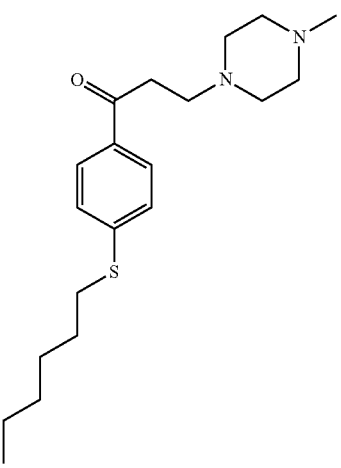
1-(4-(hexylthio)phenyl)-3-(4-methylpiperazin-1-yl)propan-1-one, Compound 14 (FT019)
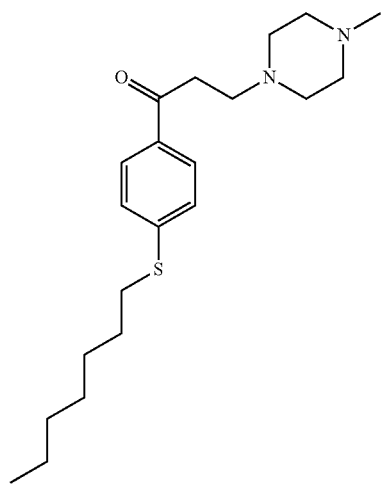
1-(4-(heptylthio)phenyl)-3-(4-methylpiperazin-1-yl)propan-1-one,
Compound 15 (GR376)
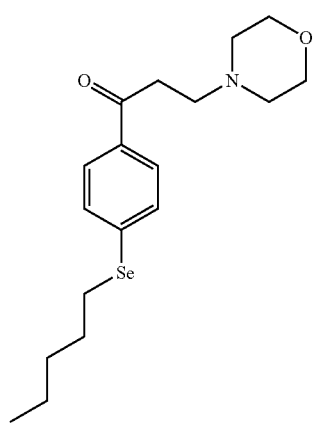
3-morpholino-1-(4-(pentylselenyl)phenyl)propan-1-one,
Compound 16 (GR377)
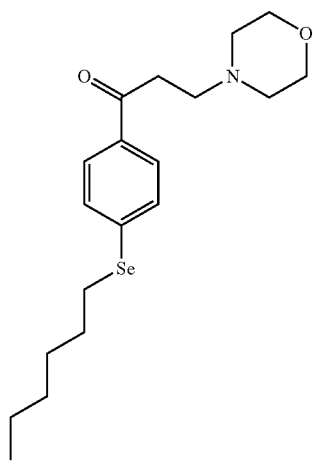
1-(4-(hexylselenyl)phenyl)-3-morpholinopropan-1-one,
Compound 17 (GR386)
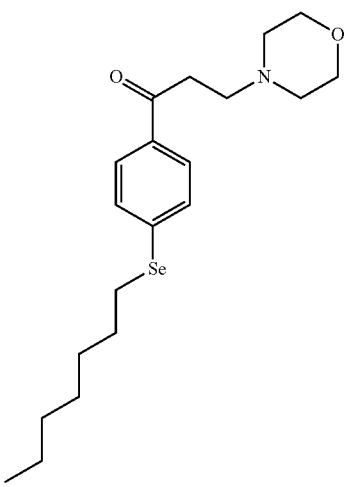
1-(4-(heptylselenyl)phenyl)-3-morpholinopropan-1-one,
Compound 18 (GR378)
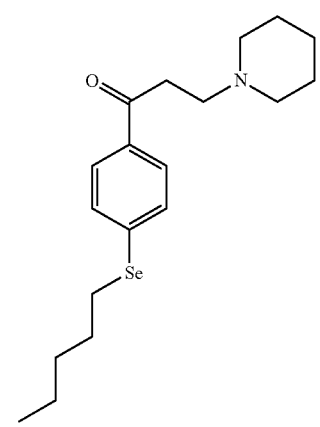
1-(4-(pentylselenyl)phenyl)-3-(piperidin-1-yl)propan-1-one,
Compound 19 (GR381)
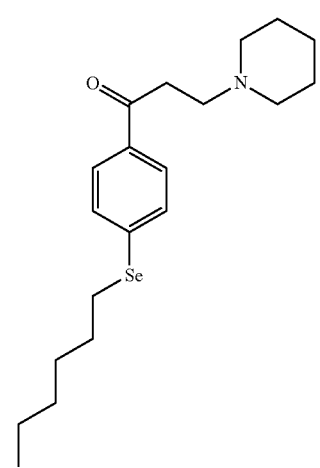
1-(4-(hexylselenyl)phenyl)-3-(piperidin-1-yl)propan-1-one, Compound 20 (GR387)
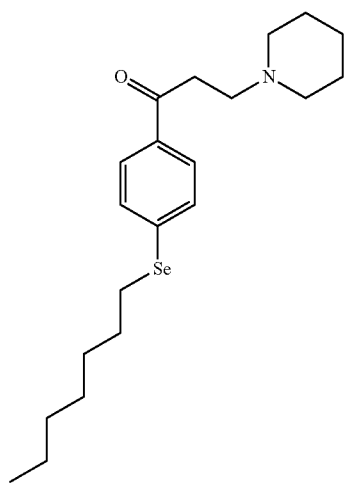
1-(4-(heptylselenyl)phenyl)-3-(piperidin-1-yl)propan-1-one,
Compound 21 (GR379)
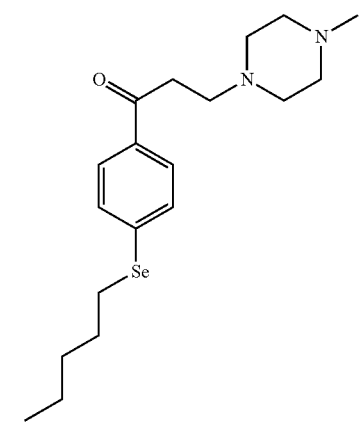
3-(4-methylpiperazin-1-yl)-1-(4-(pentylselenyl)phenyl)propan-1-one,
Compound 22 (GR383)
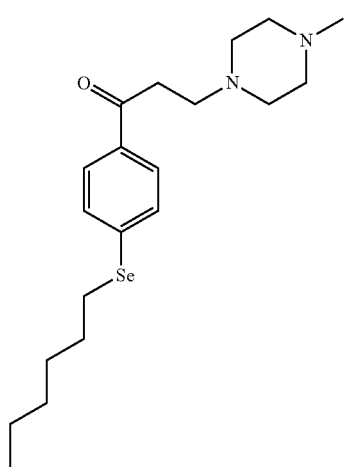
1-(4-(hexylselenyl)phenyl)-3-(4-methylpiperazin-1-yl)propan-1-one,
Compound 23 (GR388)
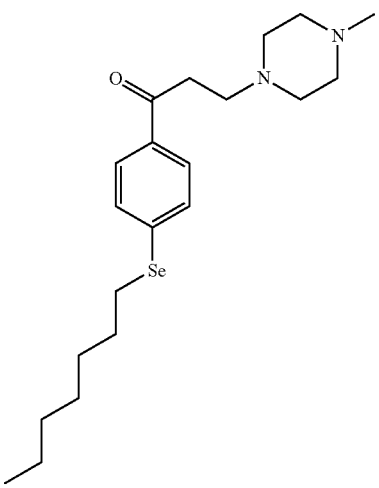
1-(4-(heptylselenyl)phenyl)-3-(4-methylpiperazin-1-yl)propan-1-one,
Compound 24 (GR390)
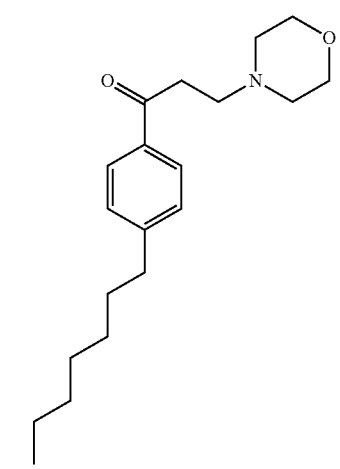
1-(4-(heptylphenyl)-3-morpholinopropan-1-one,
Compound 25 (GR391)
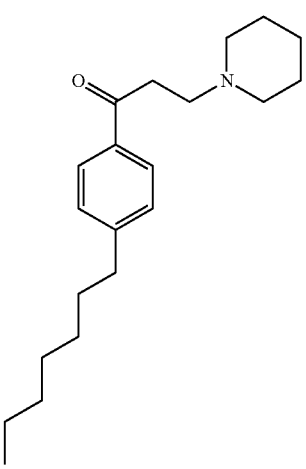
1-(4-(heptylphenyl)-3-(piperidin-1-yl)propan-1-one, and Compound 26 (GR392)

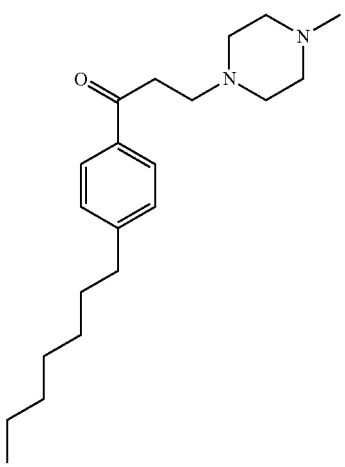

1-(4-(heptylphenyl)-3-(4-methylpiperazin-1-yl)propan-1-one.

More preferably, in the treatment of breast cancer, chronic lymphatic leukemia (LLC) or neuroblastoma, the compound of formula (I) is selected from the group consisting of:
Compound 1 (AF08), 1-(4-(hexyloxy)phenyl)-3-morpholinopropan-1-one,
Compound 3 (AF07), 1-(4-(hexyloxy)phenyl)-3-(piperidin-1-yl)propan-1-one,
Compound 4 (CC12), 1-(4-(heptyloxy)phenyl)-3-(piperidin-1-yl)propan-1-one,
Compound 5 (AI01), 1-(4-(heptyloxy)phenyl)-3-(4-methylpiperazin-1-yl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 10 (VP157), 1-(4-(hexylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
Compound 25 (GR391), 1-(4-heptylphenyl)-3-(piperidin-1-yl)propan-1-one, and
Compound 26 (GR392), 1-(4-heptylphenyl)-3-(4-methylpiperazin-1-yl)propan-1-one.

Even more preferably, in the treatment of breast cancer, chronic lymphatic leukemia (LLC) or neuroblastoma, the compound of formula (I) is selected from the group consisting of:
Compound 1 (AF08), 1-(4-(hexyloxy)phenyl)-3-morpholinopropan-1-one,
Compound 5 (AI01), 1-(4-(heptyloxy)phenyl)-3-(4-methylpiperazin-1-yl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12) 1-(4-(pentylthio)phenyl)-3-(piperidin-1-yl)propan-1-one,
Compound 10 (VP157), 1-(4-(hexylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
Compound 25 (GR391), 1-(4-heptylphenyl)-3-(piperidin-1-yl)propan-1-one, and
Compound 26 (GR392), 1-(4-heptylphenyl)-3-(4-methylpiperazin-1-yl)propan-1-one.

The inventors also synthesized new 1-phenylpropanone compounds that resulted to have apoptotic activity against tumor cells.

In another aspect, the invention concerns a 1-phenylpropanone compound of formula (I)

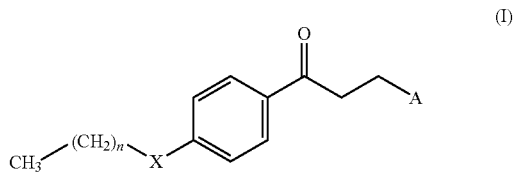

wherein:
X is a methylene group (—$CH_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a ($C_1$-$C_3$)alkyl or ($C_1$-$C_3$) acyl radical,
with the proviso that
when X is O, A is 4-methyl-1-piperazinyl, and n is equal to 6,
when X is S and n is 5, then A is 4-methyl-1-piperazinyl,
when X is Se and A is 1-piperidinyl, then n is 6,
when X is $CH_2$, n is equal to 5, and A is 4-methyl-1-piperazinyl or 4-morpholyl.

Preferably, in the 1-phenylpropanone compound of the invention, X is selected from the group consisting of S, Se or $CH_2$, more preferably it is S.

A is optionally substituted with a ($C_1$-$C_3$)alkyl or ($C_1$-$C_3$) acyl substituent.

Advantageously, the compound of the invention is a compound wherein n is 5 or 6.

The new compound of formula (I) is preferably a compound selected from the group consisting of:
Compound 5 (AI01), 1-(4-(heptyloxy)phenyl)-3-(4-methylpiperazin-1-yl)propan-1-one,
Compound 6 (MD63), 3-morpholino-1-(4-(pentylthio)phenyl)propan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 12 (FT013), 3-(4-methylpiperazin-1-yl)-1-(4-(pentylthio)phenyl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 15 (GR376), 3-morpholino-1-(4-(pentylselenyl)phenyl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 21 (GR379), 3-(4-methylpiperazin-1-yl)-1-(4-(pentylselenyl)phenyl)propan-1-one,
Compound 22 (GR383), 1-(4-(hexylselenyl)phenyl)-3-(4-methylpiperazin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
Compound 26 (GR392), 1-(4-heptylphenyl)-3-(4-methylpiperazin-1-yl)propan-1-one.

More preferably, the new compound of formula (I) is preferably a compound selected from the group consisting of:
Compound 5 (AI01), 1-(4-(heptyloxy)phenyl)-3-(4-methylpiperazin-1-yl)propan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one, and
Compound 26 (GR392), 1-(4-heptylphenyl)-3-(4-methylpiperazin-1-yl)propan-1-one.

Even more preferably, the new compound of formula (I) is preferably a compound selected from the group consisting of:
Compound 8 (FT017), 1-(4-(heptylthio)phenyl)-3-morpholinopropan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 24 (GR390), 1-(4-heptylphenyl)-3-morpholinopropan-1-one,
Compound 26 (GR392), 1-(4-heptylphenyl)-3-(4-methylpiperazin-1-yl)propan-1-one.

In a further aspect the invention concerns a compound of formula (I)

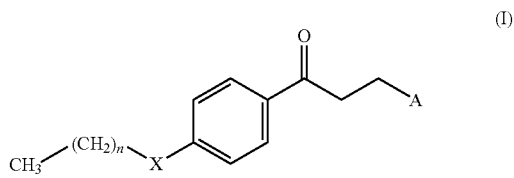

wherein:
X is a methylene group (—$CH_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a ($C_1$-$C_3$)alkyl or ($C_1$-$C_3$) acyl radical,
with the proviso that
when X is O, A is 4-methyl-1-piperazinyl and n is equal to 6,
when X is S and n is 5, then A is 4-methyl-1-piperazinyl or 4-morpholyl,
when X is Se and A is 1-piperidinyl, then n is 6,
when X is $CH_2$, n is equal to 5, and A is 4-methyl-1-piperazinyl or 4-morpholyl for use as a medicament.

Preferably, in the 1-phenylpropanone compound as a medicament of the invention, X is selected from the group consisting of S, Se or $CH_2$, more preferably it is S.

A is optionally substituted with a ($C_1$-$C_3$)alkyl or ($C_1$-$C_3$) acyl substituent.

Advantageously, the compound as a medicament of the invention is a compound wherein n is 5 or 6.

The compound of formula (I) as a medicament is preferably a compound selected from the group consisting of:
Compound 5 (AI01), 1-(4-(heptyloxy)phenyl)-3-(4-methylpiperazin-1-yl)propan-1-one,
Compound 6 (MD63), 3-morpholino-1-(4-(pentylthio)phenyl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 12 (FT013), 3-(4-methylpiperazin-1-yl)-1-(4-(pentylthio)phenyl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one, Compound 15 (GR376), 3-morpholino-1-(4-(pentylselenyl)phenyl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 21 (GR379), 3-(4-methylpiperazin-1-yl)-1-(4-(pentylselenyl)phenyl)propan-1-one,
Compound 22 (GR383), 1-(4-(hexylselenyl)phenyl)-3-(4-methylpiperazin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one, and
Compound 26 (GR392), 1-(4-heptylphenyl)-3-(4-methylpiperazin-1-yl)propan-1-one.

More preferably, the new compound of formula (I) as a medicament is preferably a compound selected from the group consisting of:
Compound 5 (AI01), 1-(4-(heptyloxy)phenyl)-3-(4-methylpiperazin-1-yl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one, and
Compound 26 (GR392), 1-(4-heptylphenyl)-3-(4-methylpiperazin-1-yl)propan-1-one.

Even more preferably, the new compound of formula (I) as a medicament is preferably a compound selected from the group consisting of:
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 24 (GR390), 1-(4-heptylphenyl)-3-morpholinopropan-1-one,
Compound 26 (GR392), 1-(4-heptylphenyl)-3-(4-methylpiperazin-1-yl)propan-1-one.

In a further aspect, the invention relates to a pharmaceutical composition comprising a compound of formula (I) as a medicament, and a pharmaceutically acceptable vehicle.

The compounds of the invention, as such or a pharmaceutically acceptable salt thereof, may be employed in medicine. They can then be combined with a pharmaceutically acceptable vehicle, and optionally suitable excipients, to obtain pharmaceutical compositions. By the term "pharmaceutically acceptable vehicle" it is meant to include solvents, technological aids, diluents, and the like that are employed in administering compounds of the invention.

Such pharmaceutical compositions may be administered by parenteral, oral, buccal, sublingual, nasal, rectal, topical, or transdermal route.

Compositions of the present invention suitable for oral administration will conveniently be in the form of discrete units, such as tablets, capsules, cachets, powders, or granules, or even as suspensions in a liquid.

The tablets may also contain suitable pharmaceutical excipients, such as pre-gelatinized starch, microcrystalline cellulose, sodium glycol starch, talc, lactose, magnesium stearate, sucrose, stearic acid, mannitol.

Compositions for parenteral administration will conveniently comprise sterile preparations.

Compositions for topical administration will conveniently be in the form of creams, pastes, oils, ointments, emulsions, foams, gels, drops, spray solutions, and transdermal patches.

In yet a further aspect, the invention concerns a compound of formula (I)

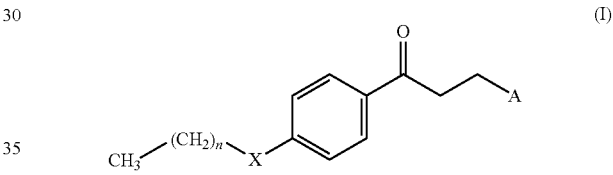

wherein:
X is a methylene group (—$CH_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a ($C_1$-$C_3$)alkyl or ($C_1$-$C_3$) acyl radical,
with the proviso that
when X is O, A is 4-methyl-1-piperazinyl or 1-piperidinyl, and n is equal to 6,
when X is C, n is 5 for use as an antitumoral agent.

Preferably, the antitumoral treatment is against breast cancer, hepatocarcinoma, chronic lymphatic leukemia (LLC) or neuroblastoma.

Preferably, in the 1-phenylpropanone compound of the invention for use as an antitumoral agent, X is selected from the group consisting of S, Se or $CH_2$, more preferably it is S.

A is optionally substituted with a ($C_1$-$C_3$)alkyl or ($C_1$-$C_3$) acyl substituent.

Advantageously, the compound of the invention for use as an antitumoral agent is a compound wherein n is 5 or 6.

Preferably, the 1-phenylpropanone compound of the invention for use as an antitumoral agent is a compound selected from the group consisting of:
Compound 4 (CC12), 1-(4-(heptyloxy)phenyl)-3-(piperidin-1-yl)propan-1-one,
Compound 5 (AI01), 1-(4-(heptyloxy)phenyl)-3-(4-methylpiperazin-1-yl)propan-1-one, Compound 6 (MD63), 3-morpholino-1-(4-(pentylthio)phenyl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 10 (VP157), 1-(4-(hexylthio)phenyl)-3-(piperidin-1-yl)propan-1-one,
Compound 11 (FT018), 1-(4-(heptylthio)phenyl)-3-(piperidin-1-yl)propan-1-one,
Compound 12 (FT013), 3-(4-methylpiperazin-1-yl)-1-(4-(pentylthio)phenyl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 15 (GR376), 3-morpholino-1-(4-(pentylselenyl)phenyl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one,
Compound 18 (GR378), 1-(4-(pentylselenyl)phenyl)-3-(piperidin-1-yl)propan-1-one,
Compound 19 (GR381), 1-(4-(hexylselenyl)phenyl)-3-(piperidin-1-yl)propan-1-one,
Compound 20 (GR387), 1-(4-(heptylselenyl)phenyl)-3-(piperidin-1-yl)propan-1-one,
Compound 21 (GR379), 3-(4-methylpiperazin-1-yl)-1-(4-(pentylselenyl)phenyl)propan-1-one,
Compound 22 (GR383), 1-(4-(hexylselenyl)phenyl)-3-(4-methylpiperazin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
Compound 25 (GR391), 1-(4-heptylphenyl)-3-(piperidin-1-yl)propan-1-one, and
Compound 26 (GR392), 1-(4-heptylphenyl)-3-(4-methylpiperazin-1-yl)propan-1-one.

More preferably it is a compound for antitumoral use selected from the group consisting of:
Compound 4 (CC12), 1-(4-(heptyloxy)phenyl)-3-(piperidin-1-yl)propan-1-one,
Compound 5 (AI01), 1-(4-(heptyloxy)phenyl)-3-(4-methylpiperazin-1-yl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 10 (VP157), 1-(4-(hexylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
Compound 25 (GR391), 1-(4-heptylphenyl)-3-(piperidin-1-yl)propan-1-one, and
Compound 26 (GR392), 1-(4-heptylphenyl)-3-(4-methylpiperazin-1-yl)propan-1-one.

Even more preferably, the compound of formula (I) for use as an antitumoral agent is selected from the group consisting of:
Compound 5 (AI01), 1-(4-(heptyloxy)phenyl)-3-(4-methylpiperazin-1-yl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 10 (VP157), 1-(4-(hexylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
Compound 25 (GR391), 1-(4-heptylphenyl)-3-(piperidin-1-yl)propan-1-one, and
Compound 26 (GR392), 1-(4-heptylphenyl)-3-(4-methylpiperazin-1-yl)propan-1-one.

According to the invention, the novel compounds or the ones for use as a medicament or as antitumoral agents, preferably and specifically for breast cancer, chronic lymphatic leukemia, or neuroblastoma, are obtained through a simple process, of easy industrial scalability, and avoiding the use of lengthy and expensive preparation steps, obtaining high yields of a stable pharmaceutically grade compound.

Now follows the experimental part for the preparation of compounds of the invention, and the assessment of the efficacy thereof, by way of illustration and not limitative of the invention.

EXPERIMENTAL PART

Example 1

Preparation of Compounds of Formula (I)
General Procedure for the Preparation of 1-Phenylpropanone Compounds of Formula (I) Wherein X is Oxygen The phenyl alkyl ether intermediate was obtained from the reaction between phenol and the appropriate 1-bromoalkane (for example, 1-bromopentane, 1-bromohexane, or 1-bromoheptane, in an amount of 1 equivalent) in acetonitrile in the presence of potassium carbonate (2 equivalents). The mixture was stirred for 5 h at room temperature, the solid thus formed was then removed by filtration, and the solvent evaporated by rotary evaporation. The obtained phenyl alkyl ether intermediate was reacted with 3-bromopropionyl chloride (2 equivalents) and aluminum trichloride (3 equivalents) in 1,2-dichloroethane in ice bath. The reaction was quenched by pouring it into water, and extracting the desired intermediate with diethyl ether. The organic layer was separated and subjected to rotary evaporation to obtain the phenyl alkyl ether derivative acylated in the para position. The intermediate thus synthesized was then treated with an appropriate cyclic amine (morpholine, piperidine or N-methyl piperazine, 2 equivalents), potassium iodide (2 equivalents) and calcium carbonate (3 equivalents) in toluene. The mixture was refluxed for 12 h. After cooling, the solid was removed by filtration, and the solvent evaporated by rotary evaporation. The residue was then dispersed into dichloromethane, and the mixture was washed with 10% sodium hydroxide solution. The organic layer was evaporated by rotary evaporation, affording the desired compound as indicated below. Yields: 68-78%.

Compound 1 (AF08), 1-(4-(hexyloxy)phenyl)-3-morpholinopropan-1-one $^1$H-NMR (400 MHz, CDCl$_3$) δ: 7.95 (d, 2H, PhH), 6.92 (d, 2H, PhH), 4.00 (t, 2H, OCH$_2$), 3.71 (m, 4H, OCH$_2$), 3.15 (t, 2H, COCH$_2$), 2.85 (t, 2H, NCH$_2$), 2.54 (m, 4H, NCH$_2$), 1.82 (m, 2H, CH$_2$), 1.4-1.2 (m, 6H, CH$_2$), 0.92 (t, 3H, CH$_3$).
$^{13}$C-NMR {1H} (100 MHz, CDCl3) δ: 196.5, 162.2, 129.3, 113.2, 76.2, 67.3, 65.9, 52.8, 52.7, 34.5, 30.5, 28.0, 24.6, 21.6, 13.0. m/z (ESI): 320.2.
Yield: 72%. Purity (HPLC): 97%.

Compound 2 (CC11), 1-(4-(heptyloxy)phenyl)-3-morpholinopropan-1-one $^1$H-NMR (400 MHz, CDCl3) δ: 7.95 (d, 2H, PhH), 6.94 (d, 2H, PhH), 4.04 (t, 2H, OCH$_2$), 3.74 (m, 4H, OCH$_2$), 3.16 (t, 2H, COCH$_2$), 2.85 (t, 2H, NCH$_2$), 2.54 (m, 4H, NCH$_2$), 1.83 (m, 2H, CH$_2$), 1.5-1.2 (m, 8H, CH$_2$), 0.92 (t, 3H, CH$_3$).
$^{13}$C-NMR {1H} (100 MHz, CDCl3) δ: 197.5, 163.2, 130.3, 129.7, 114.2, 68.3, 67.0, 53.8, 53.7, 35.6, 31.7, 29.1, 29.0, 25.9, 22.6, 14.1. m/z (ESI): 334.2.
Yield: 68%. Purity (HPLC): 97%.

Compound 3 (AF07), 1-(4-(hexyloxy)phenyl)-3-(piperidin-1-yl)propan-1-one

1H-NMR (400 MHz, CDCl3) δ: 7.80 (d, 2H, PhH), 6.94 (d, 2H, PhH), 4.04 (t, 2H, OCH$_2$), 3.18 (m, 4H, NCH$_2$), 3.11 (t, 2H, COCH$_2$), 2.82 (t, 2H, CH$_2$), 1.82 (m, 2H, CH$_2$), 1.63 (m, 4H, CH$_2$), 1.49 (m, 4H, CH$_2$), 1.37 (m, 4H, CH$_2$), 0.93 (t, 3H, CH$_3$).
$^{13}$C-NMR {1H} (100 MHz, CDCl$_3$) δ: 195.5, 161.8, 129.0, 128.5, 12.9, 75.9, 66.9, 53.3, 52.8, 30.3, 27.8, 24.6, 24.7, 21.3, 19.0, 12.8. m/z (ESI): 318.2.
Yield: 75%. Purity (HPLC): 98%.

Compound 4 (CC12), 1-(4-(heptyloxy)phenyl)-3-(piperidin-1-yl)propan-1-one $^1$H-NMR (400 MHz, CDCl3) δ: 7.81 (d, 2H, PhH), 6.92 (d, 2H, PhH), 4.01 (t, 2H, OCH$_2$), 3.18 (m, 4H, NCH$_2$), 3.10 (t, 2H, COCH$_2$), 2.83 (t, 2H, CH$_2$), 1.82 (m, 2H, CH$_2$), 1.62 (m, 6H, CH$_2$), 1.50 (m, 4H, CH$_2$), 1.32 (m, 4H, CH$_2$), 0.99 (t, 3H, CH$_3$).
$^{13}$C-NMR {1H} (100 MHz, CDCl$_3$) δ: 198.0, 163.1, 130.3, 129.8, 114.2, 68.2, 54.6, 54.2, 36.1, 31.7, 29.1, 29.0, 26.0, 25.9, 24.3, 22.6, 14.1. m/z (ESI): 332.3.
Yield: 76%. Purity (HPLC): 97%.

Compound 5 (AI01), 1-(4-(heptyloxy)phenyl)-3-(4-methylpiperazin-1-yl)propan-1-one $^1$H-NMR (400 MHz, CDCl$_3$) δ: 7.89 (d, 2H, PhH), 6.90 (d, 2H, PhH), 4.03 (t, 2H, OCH$_2$), 3.12 (t, 2H, COCH$_2$), 2.83 (t, 2H, NCH$_2$), 2.62 (m, 4H, NCH$_2$), 2.50 (m, 4H, NCH$_2$), 2.33 (s, 3H, CH$_3$), 1.81 (m, 2H, CH$_2$), 1.4-1.2 (m, 8H, CH$_2$), 0.92 (t, 3H, CH$_3$).
$^{13}$C-NMR {1H} (100 MHz, CDCl$_3$) δ: 196.2, 162.2, 129.1, 114.1, 76.9, 66.7, 65.1, 52.8, 51.1, 45.1, 32.5, 33.2, 29.4, 28.7, 24.6, 21.2, 13.1. m/z (ESI): 347.3.
Yield: 70%. Purity (HPLC): 97%.

General Procedure for the Preparation of 1-Phenylpropanone Compounds of Formula (I) Wherein X is Sulfur The phenyl alkyl thioether intermediate was obtained from the reaction between thiophenol and the appropriate 1-bromoalkane (for example, 1-bromopentane, 1-bromohexane, or 1-bromoheptane, 1 equivalent) in the presence of potassium hydroxide (2 equivalents) in ethanol at room temperature. The mixture was stirred for 5 h at room temperature, the solid thus formed was then removed by filtration, and the solvent evaporated by rotary evaporation. The obtained phenyl alkyl thioether intermediate was then reacted with 3-bromopropionyl chloride (2 equivalents) and aluminum trichloride (3 equivalents) in 1,2-dichloroethane in ice bath. The reaction was quenched by pouring it into water, and extracting the desired intermediate with diethyl ether. The organic layer was separated and subjected to rotary evaporation to obtain the phenyl alkyl thioether acylated in the para position. The intermediate thus synthesized was treated with an appropriate cyclic amine (morpholine, piperidine or N-methyl piperazine, 2 equivalents), potassium iodide (2 equivalents) and calcium carbonate (3 equivalents) in toluene. The mixture was refluxed for 12 h. After cooling, the solid was removed by filtration, and the solvent evaporated by rotary evaporation. The residue was dispersed into dichloromethane, and the mixture was washed with 10% sodium hydroxide solution. The organic layer was evaporated by rotary evaporation to afford the desired compound. Yields: 65-75%.

Compound 6 (MD63), 3-morpholino-1-(4-(pentylthio)phenyl)propan-1-one $^1$H-NMR (400 MHz, CDCl$_3$) δ: 7.83 (d, 2H, PhH), 7.28 (d, 2H, PhH), 3.69 (t, 4H, OCH$_2$), 3.12 (t, 2H, COCH$_2$), 2.97 (t, 2H, CH$_2$), 2.81 (t, 2H, SCH$_2$), 2.49 (m, 4H, NCH$_2$), 1.69 (m, 4H, CH$_2$), 1.37 (m, 2H, CH$_2$), 0.90 (t, 3H, CH$_3$).
$^{13}$C-NMR (100 MHz, CDCl$_3$) δ: 197.9, 145.1, 133.5, 128.4, 126.3, 66.8, 53.7, 53.6, 35.8, 31.8, 31.0, 28.4, 22.1, 13.8. m/z (ESI): 322.2.
Yield: 72%. Purity (HPLC): 98%.

Compound 7 (VP158), 1-(4-(hexylthio)phenyl)-3-morpholinopropan-1-one $^1$H-NMR (400 MHz, CDCl$_3$) δ: 7.84 (d, 2H, PhH), 7.19 (d, 2H, PhH), 3.69 (t, 4H, OCH$_2$), 3.10 (t, 2H, COCH$_2$), 2.98 (t, 2H, CH$_2$), 2.81 (t, 2H, SCH$_2$), 2.44 (m, 4H, NCH$_2$), 1.7-1.5 (m, 6H, CH$_2$), 1.37 (m, 2H, CH$_2$), 0.90 (t, 3H, CH$_3$).

¹³C-NMR (100 MHz, CDCl₃) δ: 197.9, 145.2, 137.1, 133.4, 128.8, 68.9, 53.7, 35.7, 33.6, 31.9, 31.3, 30.5, 29.1, 28.5, 22.5. m/z (ESI): 336.2.

Yield: 69%. Purity (HPLC): 97%.

Compound 8 (FT17), 1-(4-(heptylthio)phenyl)-3-morpholinopropan-1-one

¹H-NMR (400 MHz, CDCl₃) δ: 7.82 (d, 2H, PhH), 7.22 (d, 2H, PhH), 3.66 (t, 4H, OCH₂), 3.12 (t, 2H, COCH₂), 2.92 (t, 2H, CH₂), 2.79 (t, 2H, SCH₂), 2.44 (m, 4H, NCH₂), 1.6-1.5 (m, 8H, CH₂), 1.34 (m, 2H, CH₂), 0.98 (t, 3H, CH₃).

¹³C-NMR (100 MHz, CDCl₃) δ: 197.7, 145.1, 136.1, 133.2, 128.9, 69.9, 54.7, 36.7, 35.4, 33.6, 31.9, 31.0, 30.1, 29.4, 28.4, 22.5. m/z (ESI): 350.2.

Yield: 65%. Purity (HPLC): 97%.

Compound 9 (MC12), 1-(4-(pentylthio)phenyl)-3-(piperidin-1-yl)propan-1-one

¹H-NMR (400 MHz, CDCl₃) δ: 7.74 (d, 2H, PhH), 6.94 (d, 2H, PhH), 3.13 (m, 4H, NCH₂), 3.11 (t, 2H, COCH₂), 3.04 (t, 2H, SCH₂), 2.72 (t, 2H, CH₂), 1.82 (m, 2H, CH₂), 1.63 (m, 4H, CH₂), 1.49 (m, 2H, CH₂), 1.37 (m, 2H, CH₂), 0.93 (t, 3H, CH₃).

¹³C-NMR {1H} (100 MHz, CDCl₃) δ: 198.0, 163.1, 130.3, 129.8, 14.2, 68.2, 54.6, 54.2, 34.1, 31.7, 29.3, 26.7, 24.3, 22.6, 14.1 m/z (ESI): 320.2.

Yield: 72%. Purity (HPLC): 98%.

Compound 10 (VP157), 1-(4-(hexylthio)phenyl)-3-(piperidin-1-yl)propan-1-one

¹H-NMR (400 MHz, CDCl₃) δ: 7.70 (d, 2H, PhH), 6.94 (d, 2H, PhH), 3.12 (m, 4H, NCH₂), 3.09 (t, 2H, COCH₂), 3.04 (t, 2H, SCH₂), 2.71 (t, 2H, CH₂), 1.81 (m, 2H, CH₂), 1.6-1.5 (m, 4H, CH₂), 1.49 (m, 4H, CH₂), 1.37 (m, 2H, CH₂), 0.93 (t, 3H, CH₃).

¹³C-NMR (100 MHz, CDCl₃) δ: 198.2, 145.1, 133.4, 128.8, 126.3, 54.5, 53.9, 45.1, 36.0, 33.6, 31.9, 31.3, 28.9, 28.5, 25.7, 22.5. m/z (ESI): 334.2.

Yield: 71%. Purity (HPLC): 97%.

Compound 11 (FT018), 1-(4-(heptylthio)phenyl)-3-(piperidin-1-yl)propan-1-one

¹H-NMR (400 MHz, CDCl₃) δ: 7.72 (d, 2H, PhH), 6.93 (d, 2H, PhH), 3.11 (m, 4H, NCH₂), 3.08 (t, 2H, COCH₂), 3.00 (t, 2H, SCH₂), 2.72 (t, 2H, CH₂), 1.81 (m, 2H, CH₂), 1.6-1.5 (m, 4H, CH₂), 1.49 (m, 6H, CH₂), 1.33 (m, 2H, CH₂), 0.90 (t, 3H, CH₃).

¹³C-NMR (100 MHz, CDCl₃) δ: 197.9, 145.0, 136.0, 133.1, 128.8, 69.9, 62.3, 54.7, 36.2, 35.8, 33.5, 31.8, 31.1, 30.2, 29.7, 28.2, 22.4. m/z (ESI): 349.2.

Yield: 68%. Purity (HPLC): 97%.

Compound 12 (FT013), 3-(4-methylpiperazin-1-yl)-1-(4-(pentylthio)phenyl)propan-1-one ¹H-NMR (400 MHz, CDCl₃) δ: 7.75 (d, 2H, PhH), 6.90 (d, 2H, PhH), 3.16 (t, 2H, COCH₂), 3.03 (t, 2H, SCH₂), 2.84 (t, 2H, NCH₂), 2.60 (m, 4H, NCH₂), 2.51 (m, 4H, NCH₂), 2.23 (s, 3H, CH₃), 1.82 (m, 2H, CH₂), 1.4-1.2 (m, 4H, CH₂), 0.97 (t, 3H, CH₃).

¹³C-NMR {1H} (100 MHz, CDCl₃) δ: 193.2, 161.2, 132.3, 111.6, 75.3, 67.9, 65.1, 52.7, 51.6, 45.2, 34.5, 31.6, 29.2, 22.2, 13.8. m/z (ESI): 335.2.

Yield: 75%. Purity (HPLC): 98%.

Compound 13 (FT016), 1-(4-(hexylthio)phenyl)-3-(4-methylpiperazin-1-yl)propan-1-one ¹H-NMR (400 MHz, CDCl₃) δ: 7.75 (d, 2H, PhH), 6.92 (d, 2H, PhH), 3.15 (t, 2H, COCH₂), 3.03 (t, 2H, SCH₂), 2.84 (t, 2H, NCH₂), 2.64 (m, 4H, NCH₂), 2.52 (m, 4H, NCH₂), 2.27 (s, 3H, CH₃), 1.82 (m, 2H, CH₂), 1.4-1.2 (m, 6H, CH₂), 0.92 (t, 3H, CH₃).

¹³C-NMR {1H} (100 MHz, CDCl₃) δ: 196.1, 164.1, 130.3, 112.1, 75.2, 68.9, 65.3, 52.1, 51.7, 45.5, 34.9, 31.2, 28.0, 23.2, 21.2, 14.6. m/z (ESI): 349.2.

Yield: 72%. Purity (HPLC): 97%.

Compound 14 (FT19), 1-(4-(heptylthio)phenyl)-3-(4-methylpiperazin-1-yl)propan-1-one ¹H-NMR (400 MHz, CDCl₃) δ: 7.78 (d, 2H, PhH), 6.90 (d, 2H, PhH), 3.11 (t, 2H, COCH₂), 3.01 (t, 2H, SCH₂), 2.87 (t, 2H, NCH₂), 2.63 (m, 4H, NCH₂), 2.52 (m, 4H, NCH₂), 2.23 (s, 3H, CH₃), 1.82 (m, 2H, CH₂), 1.4-1.2 (m, 8H, CH₂), 0.99 (t, 3H, CH₃).

¹³C-NMR {1H} (100 MHz, CDCl₃) δ: 190.3, 168.2, 130.1, 111.4, 75.4, 69.0, 65.4, 52.8, 51.2, 49.3, 34.8, 31.0, 29.9, 28.4, 23.7, 21.2, 13.9. m/z (ESI): 363.2.

Yield: 70%. Purity (HPLC): 97%.

General Procedure for the Preparation of 1-phenylpropanone Compounds of Formula (I) Wherein X is Selenium An appropriate amount of diphenyl diselenide was dissolved in ethanol, and the obtained solution was placed in an ice bath. Sodium borohydride (4 equivalents) was added cautiously, while keeping it cold and under stirring. After 20 minutes, the appropriate 1-bromoalkane (for example, 1-bromopentane, 1-bromohexane, or 1-bromoheptane, 1 equivalent) was added to the mixture. After 5 h, the reaction was quenched by adding water, and ethanol was removed by rotary evaporation. The resulting residue was dispersed in diethyl ether, and the organic layer was washed with water. Diethyl ether was removed by rotary evaporation to obtain phenyl alkyl selenoether. Such an intermediate was reacted with 3-bromopropionyl chloride (2 equivalents) and aluminum trichloride (3 equivalents) in 1,2-dichloroethane in an ice bath. The reaction was quenched by pouring it into water, and extracting the desired intermediate with diethyl ether. The organic layer was separated and subjected to rotary evaporation to obtain the phenyl alkyl selenoether acylated in the para position. The intermediate thus synthesized was treated with an appropriate cyclic amine (morpholine, piperidine or N-methyl piperazine, 2 equivalents), potassium iodide (2 equivalents) and calcium carbonate (3 equivalents) in toluene. The mixture was refluxed for 12 h. After cooling, the solid was removed by filtration, and the solvent evaporated by rotary evaporation. The residue was then dispersed into dichloromethane, and the mixture was washed with 10% sodium hydroxide solution. The organic layer was evaporated by rotary evaporation to obtain the desired compound. Yields: 72-80%.

Compound 15 (GR376), 3-morpholino-1-(4-(pentylselenyl)phenyl)propan-1-one

¹H-NMR (400 MHz, CDCl3) δ: 7.76 (d, 2H, PhH), 7.28 (d, 2H, PhH), 3.69 (t, 4H, OCH₂), 3.12 (t, 2H, COCH₂), 3.01

(t, 2H, SeCH$_2$), 2.92 (t, 2H, NCH$_2$), 2.49 (m, 4H, NCH$_2$), 1.69 (m, 4H, CH$_2$), 1.37 (m, 2H, CH$_2$), 0.90 (t, 3H, CH$_3$).
$^{13}$C-NMR (100 MHz, CDCl$_3$) δ: 196.2, 145.4, 133.5, 128.2, 126.3, 66.7, 53.2, 53.1, 35.2, 31.2, 31.1, 28.7, 22.2, 13.9. m/z (ESI): 370.2.
Yield: 73%. Purity (HPLC): 98%.

Compound 16 (GR377), 1-(4-(hexylselenyl)phenyl)-3-morpholinopropan-1-one $^1$H-NMR (400 MHz, CDCl$_3$) δ: 7.75 (d, 2H, PhH), 7.29 (d, 2H, PhH), 3.64 (t, 4H, OCH$_2$), 3.12 (t, 2H, COCH$_2$), 3.02 (t, 2H, SeCH$_2$), 2.91 (t, 2H, NCH$_2$), 2.49 (m, 4H, NCH$_2$), 1.69 (m, 6H, CH$_2$), 1.37 (m, 2H, CH$_2$), 0.90 (t, 3H, CH$_3$).
$^{13}$C-NMR (100 MHz, CDCl$_3$) δ: 196.2, 145.4, 132.5, 128.2, 125.2, 66.7, 53.6, 53.1, 35.1, 31.2, 31.1, 28.7, 25.2, 22.2, 13.9. m/z (ESI): 384.1.
Yield: 79%. Purity (HPLC): 97%.

Compound 17 (GR386), 1-(4-(heptylselenyl)phenyl)-3-morpholinopropan-1-one $^1$H-NMR (400 MHz, CDCl$_3$) δ: 7.73 (d, 2H, PhH), 7.29 (d, 2H, PhH), 3.62 (t, 4H, OCH$_2$), 3.12 (t, 2H, COCH$_2$), 3.03 (t, 2H, SeCH$_2$), 2.91 (t, 2H, NCH$_2$), 2.47 (m, 4H, NCH$_2$), 1.7-1.5 (m, 8H, CH$_2$), 1.38 (m, 2H, CH$_2$), 0.91 (t, 3H, CH$_3$).
$^{13}$C-NMR (100 MHz, CDCl$_3$) δ: 198.1, 145.2, 132.1, 128.6, 125.1, 66.8, 53.2, 49.5, 35.3, 31.0, 31.2, 28.9, 25.1, 22.0, 14.2. m/z (ESI): 398.2.
Yield: 80%. Purity (HPLC): 97%.

Compound 18 (GR378), 1-(4-(pentylselenyl)phenyl)-3-(piperidin-1-yl)propan-1-one $^1$H-NMR (400 MHz, CDCl$_3$) δ: 7.74 (d, 2H, PhH), 6.94 (d, 2H, PhH), 3.15 (m, 4H, NCH$_2$), 3.11 (t, 2H, COCH$_2$), 3.01 (m, 2H, SeCH$_2$), 2.82 (t, 2H, CH$_2$), 1.80 (m, 2H, CH$_2$), 1.63 (m, 2H, CH$_2$), 1.46 (m, 4H, CH$_2$), 1.37 (m, 2H, CH$_2$), 0.93 (t, 3H, CH$_3$).
$^{13}$C-NMR {1H} (100 MHz, CDCl$_3$) δ: 198.0, 162.1, 131.2, 129.3, 140.1, 68.1, 53.2, 54.6, 34.2, 30.5, 29.2, 26.7, 24.2, 22.1, 14.0. m/z (ESI): 368.1.
Yield: 72%. Purity (HPLC): 97%.

Compound 19 (GR381), 1-(4-(hexylselenyl)phenyl)-3-(piperidin-1-yl)propan-1-one $^1$H-NMR (400 MHz, CDCl$_3$) δ: 7.74 (d, 2H, PhH), 6.92 (d, 2H, PhH), 3.11 (m, 4H, NCH$_2$) 3.08 (t, 2H, COCH$_2$), 3.02 (m, 2H, SeCH$_2$), 2.81 (t, 2H, CH$_2$), 1.79 (m, 2H, CH$_2$), 1.62 (m, 4H, CH$_2$), 1.45 (m, 6H, CH$_2$), 1.32 (m, 2H, CH$_2$), 0.91 (t, 3H, CH$_3$).
$^{13}$C-NMR {1H} (100 MHz, CDCl$_3$) δ: 195.2, 161.6, 132.1, 130.2, 141.1, 67.4, 53.1, 51.4, 38.2, 33.1, 30.5, 29.8, 26.1, 23.9, 19.8, 14.1. m/z (ESI): 382.2.
Yield: 76%. Purity (HPLC): 98%.

Compound 20 (GR387), 1-(4-(heptylselenyl)phenyl)-3-(piperidin-1-yl)propan-1-one $^1$H-NMR (400 MHz, CDCl$_3$) δ: 7.74 (d, 2H, PhH), 6.92 (d, 2H, PhH), 3.12 (m, 4H, NCH$_2$), 3.09 (t, 2H, COCH$_2$), 3.01 (t, 2H, SeCH$_2$), 2.81 (t, 2H, CH$_2$), 1.79 (m, 4H, CH$_2$), 1.7-1.4 (m, 10H, CH$_2$), 0.91 (t, 3H, CH$_3$).
$^{13}$C-NMR {1H} (100 MHz, CDCl$_3$) δ: 191.2, 162.2, 131.5, 132.1, 142.2, 68.2, 51.0, 50.4, 38.1, 35.2, 32.4, 31.5, 29.0, 26.2, 23.8, 19.7, 14.2. m/z (ESI): 396.2.
Yield: 75%. Purity (HPLC): 96%.

Compound 21 (GR379), 3-(4-methylpiperazin-1-yl)-1-(4-(pentylselenyl)phenyl)propan-1-one $^1$H-NMR (400 MHz, CDCl$_3$) δ: 7.75 (d, 2H, PhH), 6.90 (d, 2H, PhH), 3.16 (t, 2H, COCH$_2$), 3.01 (t, 2H, SeCH$_2$), 2.84 (t, 2H, NCH$_2$), 2.60 (m, 4H, NCH$_2$), 2.51 (m, 4H, NCH$_2$), 2.21 (s, 3H, CH$_3$), 1.82 (m, 2H, CH$_2$), 1.4-1.2 (m, 4H, CH$_2$), 0.97 (t, 3H, CH$_3$).
$^{13}$C-NMR {1H} (100 MHz, CDCl$_3$) δ: 195.8, 161.1, 132.2, 111.6, 75.2, 68.1, 64.2, 51.7, 51.5, 45.1, 33.2, 31.4, 29.1, 22.1, 14.8. m/z (ESI): 383.2.
Yield: 72%. Purity (HPLC): 97%.

Compound 22 (GR383), 1-(4-(hexylselenyl)phenyl)-3-(4-methylpiperazin-1-yl)propan-1-one $^1$H-NMR (400 MHz, CDCl$_3$) δ: 7.74 (d, 2H, PhH), 6.91 (d, 2H, PhH), 3.13 (t, 2H, COCH$_2$), 3.01 (t, 2H, SeCH$_2$), 2.81 (t, 2H, NCH$_2$), 2.60 (m, 4H, NCH$_2$), 2.48 (m, 4H, NCH$_2$), 2.22 (s, 3H, CH$_3$), 1.81 (m, 2H, CH$_2$), 1.5-1.2 (m, 6H, CH$_2$), 0.93 (t, 3H, CH$_3$).
$^{13}$C-NMR {1H} (100 MHz, CDCl$_3$) δ: 193.2, 161.0, 132.0, 111.5, 75.1, 68.4, 64.9, 52.9, 51.0, 45.2, 37.1, 33.1, 31.7, 29.1, 22.0, 13.8. m/z (ESI): 397.2.
Yield: 79%. Purity (HPLC): 98%.

Compound 23 (GR388), 1-(4-(heptylselenyl)phenyl)-3-(4-methylpiperazin-1-yl)propan-1-one $^1$H-NMR (400 MHz, CDCl$_3$) δ: 7.74 (d, 2H, PhH), 6.91 (d, 2H, PhH), 3.13 (t, 2H, COCH$_2$), 3.01 (t, 2H, SeCH$_2$), 2.81 (t, 2H, NCH$_2$), 2.60 (m, 4H, NCH$_2$), 2.48 (m, 4H, NCH$_2$), 2.22 (s, 3H, CH$_3$), 1.81 (m, 2H, CH$_2$), 1.5-1.2 (m, 8H, CH$_2$), 0.93 (t, 3H, CH$_3$).
$^{13}$C-NMR {1H} (100 MHz, CDCl$_3$) δ: 196.4, 160.2, 131.2, 111.2, 75.3, 68.2, 64.3, 52.1, 51.9, 45.1, 37.5, 33.3, 32.7, 31.4, 29.8, 22.2, 13.9. m/z (ESI): 411.2.
Yield: 76%. Purity (HPLC): 97%.

General Procedure for the Preparation of 1-phenylpropanone Compounds of Formula (I) Wherein X is Methylene, CH$_2$ The appropriate alkylbenzene (for example, pentylbenzene, hexylbenzene, or heptylbenzene) was reacted with 3-bromopropionyl chloride (2 equivalents) and aluminum trichloride (3 equivalents) in 1,2-dichloroethane in ice bath. The reaction was quenched by pouring it into water, and extracting the desired intermediate with diethyl ether. The organic layer was separated and subjected to rotary evaporation. The intermediate thus synthesized was then treated with an appropriate cyclic amine (morpholine, piperidine or N-methyl piperazine, 2 equivalents), potassium iodide (2 equivalents) and calcium carbonate (3 equivalents) in toluene. The mixture was refluxed for 12 h. After cooling, the solid was removed by filtration, and the solvent evaporated by rotary evaporation. The residue was dispersed into dichloromethane, and the mixture was washed with 10% sodium hydroxide solution. The organic layer was evaporated by rotary evaporation to afford the desired compound. Yields: 61-75%.

Compound 24 (GR390), 1-(4-heptylphenyl)-3-morpholinopropan-1-one $^1$H-NMR (400 MHz, CDCl$_3$) δ: 7.75 (d, 2H, PhH), 7.08 (d, 2H, PhH), 3.69 (t, 4H, OCH$_2$), 3.12 (t, 2H, COCH$_2$), 2.87

(t, 2H, NCH$_2$), 2.62 (t, 2H, PhCH$_2$), 2.48 (m, 4H, NCH$_2$), 1.74 (m, 6H, CH$_2$), 1.30 (m, 4H, CH$_2$), 0.90 (t, 3H, CH$_3$).

$^{13}$C-NMR (100 MHz, CDCl$_3$) δ: 191.5, 157.2, 143.1, 131.6, 124.3, 67.5, 53.2, 51.4, 34.3, 32.0, 31.3, 28.4, 25.6, 23.0, 22.8, 14.1. m/z (ESI): 318.2.

Yield: 61%. Purity (HPLC): 97%.

Compound 25 (GR391), 1-(4-heptylphenyl)-3-(piperidin-1-yl)propan-1-one $^1$H-NMR (400 MHz, CDCl$_3$) δ: 7.74 (d, 2H, PhH), 6.91 (d, 2H, PhH), 3.09 (t, 2H, COCH$_2$), 2.99 (m, 4H, NCH$_2$), 2.55 (t, 2H, PhCH$_2$), 2.84 (t, 2H, CH$_2$), 1.75 (m, 4H, CH$_2$), 1.62 (m, 4H, CH$_2$), 1.41 (m, 6H, CH$_2$), 1.31 (m, 4H, CH$_2$), 0.96 (t, 3H, CH$_3$).

$^{13}$C-NMR (100 MHz, CDCl$_3$) δ: 190.4, 157.5, 142.2, 133.1, 125.2, 68.7, 54.1, 52.2, 37.0, 32.1, 31.5, 29.7, 28.4, 27.2, 25.0, 24.2, 13.5. m/z (ESI): 316.3.

Yield: 72%. Purity (HPLC): 98%.

Compound 26 (GR392), 1-(4-heptylphenyl)-3-(4-methylpiperazin-1-yl)propan-1-one $^1$H-NMR (400 MHz, CDCl$_3$) δ: 7.72 (d, 2H, PhH), 6.90 (d, 2H, PhH), 3.12 (t, 2H, COCH$_2$), 2.82 (t, 2H, NCH$_2$), 2.62 (m, 4H, NCH$_2$), 2.49 (t, 2H, PhCH$_2$), 2.43 (m, 4H, NCH$_2$), 2.21 (s, 3H, CH$_3$), 1.81 (m, 2H, CH$_2$), 1.5-1.2 (m, 8H, CH$_2$), 0.93 (t, 3H, CH$_3$).

$^{13}$C-NMR {1H} (100 MHz, CDCl$_3$) δ: 196.3, 161.4, 131.3, 111.6, 78.2, 67.1, 66.2, 54.2, 51.7, 45.2, 34.5, 33.3, 31.7, 31.5, 29.7, 21.2, 15.1. m/z (ESI): 331.3.

Yield: 75%. Purity (HPLC): 97%.

Example 2

Evaluation of the Proapoptotic Effect on Tumor Cells In Vitro

Flow cytofluorometry was used to evaluate the ability of some compounds of the invention to induce cell death, with particular reference to apoptosis. This latter phenomenon is characterized by morphological modification of the plasmatic membrane as a result of the translocation of the phospholipid phosphatidylserine (PS) in the plasmatic membrane from the cytoplasmic side to the outer surface of the cell. In the presence of calcium ions, the annexin V protein exhibits high affinity for PS, becoming a reliable marker for apoptosis detection. Annexin is detected because it is conjugated to a specific fluorochrome, thus allowing to distinguish apoptosis from necrotic phenomena, which are instead measured by the fluorescent dye propidium iodide, which penetrates freely in the cell having a damaged plasmatic membrane.

Both primary lymphocytic tumor cells taken from patients with chronic lymphatic leukemia (LLC) and humanized cell lines of neuroblastoma (SK-N-BE), hepatocarcinoma (HepG2 and HUH7.5) and breast cancer (MDA-MB-231) were used.

HepG2 (2×10$^5$ cells per well), HUH7.5 and MDA-MB-231 (1.5×10$^5$ cells per well) cells were seeded on a 6-well plate in Dulbecco's Modified Eagle Medium (DMEM), 10% FBS and cultured at 37° C. in a 5% CO$_2$ atmosphere. After 24 hours, the medium was removed and replaced by DMEM containing the test compounds, previously dissolved in 100% dimethylsulfoxide, and diluted such that the final concentration of the same in cell incubation solutions was 0.5% (v/v). After 30 minutes incubation, 10% FBS was added, and the cells were incubated for 24 hours, then detached with trypsin, and analyzed by cytofluorimeter. LLC cells (1×10$^6$ cells per well) were seeded and cultured on 12-well plates in RPMI-1640 medium, 10% FBS, at 37° C. in a humified atmosphere containing 5% CO$_2$. To this medium, test compounds were added, and incubation was carried out for 24 hours, after which time the cells were analyzed by cytofluorimeter.

Leukemic lymphocytes were isolated, following heparinized venous withdrawal from peripheral blood of LLC patients, diluted with saline in a 1:3 ratio, layered on a Ficoll/Hypaque (F/H) density gradient, centrifuged at 900 rpm for 20 minutes, at 20° C. without brakes. Mononuclear cells and platelets, concentrating on top of the F/H gradient, were separated after 2 further washings, with centrifugation at 400 rpm at room temperature. The mononuclear cells thus obtained were washed 3 times with PBS, centrifuged for 10 minutes at 400 rpm, at 20° C. with brakes, and resuspended in RPMI 1640.

In most LLC cases, the percentage of leukemic B cells was higher than 85% with respect to all mononuclear cells from peripheral blood.

The results obtained by cytofluorometry from three separate experiments executed in triplicate were tabulated, estimating the concentration required to cause 50% apoptosis (IC$_{50}$), and standard deviation. The results are shown in Table 1 below.

TABLE 1

| | IC$_{50}$ ± S.D. (μM) | | | | |
|---|---|---|---|---|---|
| Compound | LLC | SK-N-BE | HepG2 | HUH7.5 | MDA-MB-231 |
| 1 (AF08) | 1.61 ± 0.10 | 1.85 ± 0.09 | 1.67 ± 0.15 | 1.58 ± 0.07 | 1.61 ± 0.08 |
| 2 (CC11) | 1.62 ± 0.15 | 1.64 ± 0.09 | 1.55 ± 0.13 | 1.58 ± 0.10 | 1.61 ± 0.07 |
| 3 (AF07) | 2.53 ± 0.15 | 3.00 ± 0.17 | 3.07 ± 0.09 | 2.75 ± 0.09 | 2.60 ± 0.10 |
| 4 (CC12) | 3.03 ± 0.07 | 2.93 ± 0.08 | 3.00 ± 0.15 | 2.78 ± 0.13 | 3.01 ± 0.15 |
| 5 (AI01) | 1.45 ± 0.06 | 1.55 ± 0.10 | 1.60 ± 0.05 | 1.61 ± 0.08 | 1.48 ± 0.09 |
| 6 (MD63) | 8.50 ± 0.08 | 8.20 ± 0.10 | 8.00 ± 0.14 | 8.25 ± 0.12 | 8.00 ± 0.07 |
| 7 (VP158) | 0.50 ± 0.20 | 0.53 ± 0.09 | 0.49 ± 0.11 | 0.56 ± 0.20 | 0.50 ± 0.20 |
| 8 (FT017) | 0.55 ± 0.09 | 0.60 ± 0.05 | 0.57 ± 0.08 | 0.63 ± 0.08 | 0.66 ± 0.12 |
| 9 (MC12) | 1.75 ± 0.04 | 1.85 ± 0.14 | 1.66 ± 0.10 | 1.73 ± 0.09 | 1.80 ± 0.06 |
| 10 (VP157) | 1.87 ± 0.07 | 1.67 ± 0.05 | 1.70 ± 0.05 | 1.80 ± 0.11 | 1.80 ± 0.09 |
| 11 (FT018) | 0.50 ± 0.04 | 0.54 ± 0.09 | 0.59 ± 0.01 | 0.49 ± 0.07 | 0.56 ± 0.06 |
| 12 (FT013) | 12.20 ± 0.11 | 13.17 ± 0.12 | 12.95 ± 0.05 | 14.54 ± 0.12 | 11.85 ± 0.07 |
| 13 (FT016) | 0.65 ± 0.01 | 0.67 ± 0.09 | 0.59 ± 0.06 | 0.60 ± 0.12 | 0.65 ± 0.01 |
| 14 (FT019) | 0.44 ± 0.06 | 0.45 ± 0.07 | 0.50 ± 0.09 | 0.52 ± 0.10 | 0.47 ± 0.10 |
| 15 (GR376) | 14.22 ± 0.17 | 15.71 ± 0.13 | 11.11 ± 0.07 | 12.20 ± 0.08 | 13.86 ± 0.14 |
| 16 (GR377) | 2.53 ± 0.09 | 2.47 ± 0.06 | 2.62 ± 0.08 | 2.60 ± 0.10 | 2.58 ± 0.09 |

TABLE 1-continued

| Compound | IC$_{50}$ ± S.D. (μM) | | | | |
|---|---|---|---|---|---|
| | LLC | SK-N-BE | HepG2 | HUH7.5 | MDA-MB-231 |
| 17 (GR386) | 0.55 ± 0.04 | 0.50 ± 0.06 | 0.60 ± 0.07 | 0.50 ± 0.10 | 0.55 ± 0.07 |
| 18 (GR378) | 8.50 ± 0.15 | 8.00 ± 0.10 | 7.50 ± 0.15 | 8.30 ± 0.08 | 7.90 ± 0.10 |
| 19 (GR381) | 10.10 ± 0.08 | 11.65 ± 0.06 | 12.48 ± 0.12 | 11.98 ± 0.11 | 13.01 ± 0.12 |
| 20 (GR387) | 1.70 ± 0.05 | 1.68 ± 0.13 | 1.74 ± 0.05 | 1.73 ± 0.09 | 1.75 ± 0.10 |
| 21 (GR379) | 14.16 ± 0.09 | 13.88 ± 0.13 | 15.57 ± 0.03 | 13.60 ± 0.09 | 14.23 ± 0.14 |
| 22 (GR383) | 8.15 ± 0.07 | 8.20 ± 0.07 | 8.10 ± 0.10 | 8.00 ± 0.06 | 8.10 ± 0.07 |
| 23 (GR388) | 1.77 ± 0.05 | 1.75 ± 0.09 | 1.70 ± 0.05 | 1.69 ± 0.08 | 1.70 ± 0.09 |
| 24 (GR390) | 0.50 ± 0.15 | 0.50 ± 0.17 | 0.50 ± 0.08 | 0.50 ± 0.065 | 0.55 ± 0.08 |
| 25 (GR391) | 1.50 ± 0.08 | 1.60 ± 0.10 | 1.55 ± 0.09 | 1.50 ± 0.10 | 1.65 ± 0.75 |
| 26 (GR392) | 0.85 ± 0.06 | 0.75 ± 0.13 | 0.80 ± 0.07 | 0.95 ± 0.06 | 0.90 ± 0.05 |

As shown in Table 1, the exposure of cells to the compounds reveals that:
the ideal alkyl chain is represented by 6 or 7 carbon atoms, thus n is preferably 5 or 6;
for compound with heteroatom represented by Se, a higher efficacy is observed when the carbon chain contains 7 C atoms, i.e. with n equal to 6;
the heteroatom conferring highest efficacy to the molecules is S, equally capable of inducing apoptosis irrespective from the piperidine, morpholine, and methylpiperazine groups;
in compounds wherein the heteroatom is not S, the morpholine group is the one conferring a more effective apoptotic action.

In addition, as discussed above, the two articles cited in the name of D. Ju et al. discuss the properties of dyclonine, a compound analogous to some compounds of the present invention, but with an alkoxyl chain of only 4 carbon atoms. These articles highlight the role of dyclonine solely as enhancer of the proteasome inhibitors effect in inducing apoptosis in breast cancer and multiple myeloma cells, and show efficacy in the induction of caspase-dependent apoptosis (IC$_{50}$ values) only at concentration in the range 15-30 μM, much higher than the concentrations to which the compounds of the present invention are active (IC$_{50}$ values from 0.55 up to a maximum of 14.23 μM, with most of the compounds showing IC$_{50}$ values lower than 3).

Example 3

Evaluation of the Immunosuppressive Effect of the Compounds of the Invention

As discussed in the introduction, the compound FTY720 exerts a cytotoxic action on tumor cells, while maintaining the molecular mechanism underlying the immunosuppressive effect that consists in the degradation of the S1P receptor. In order to evaluate whether this mechanism, undesirable for a potential use in antitumoral treatments, persisted in the presence of compounds of the present invention, some of these were tested by comparing them with FTY720 under the same conditions. To this end, LLC cells (5×10$^5$ per well) were seeded and cultured on 12-well plates in RPMI-1640 medium, 10% FBS, at 37° C. in a humidified atmosphere containing 5% CO$_2$, adding to the culture the various test compounds. Incubation was conducted for discrete times, at the end of which the cells were lysed to submit the protein content to Western blot analysis with antibodies that specifically recognize the S1P1 receptor. The results shown in FIG. 1 clearly show that FTY720 induces a rapid decrease of S1P1 receptor, clear already at 3 hours and even more significant after 12 hours of incubation (S1P1 concentration decrease is the cause of immunosuppression); conversely, the compounds of the invention tested leave unchanged the expression profile of the same receptor at all time points of the test.

The invention claimed is:

1. A method for the treatment of breast cancer, chronic lymphatic leukemia or neuroblastoma, comprising the step of administering a 1-phenylpropanone compound of formula (I)

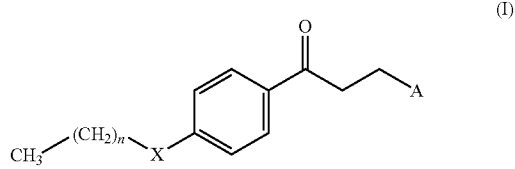

or a pharmaceutically acceptable salt thereof
wherein:
X is a methylene group (—CH$_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a (C$_1$-C$_3$)alkyl or (C$_1$-C$_3$)acyl radical,
with the proviso that
when X is O, A is 4-methyl-1-piperazinyl, and n is equal to 6,
when X is S and n is 5, then A is 4-methyl-1-piperazinyl,
when X is Se and A is 1-piperidinyl, then n is 6,
when X is CH$_2$, n is equal to 5, and A is 4-methyl-1-piperazinyl or 4-morpholyl.

2. The method of claim 1, wherein X is S, Se or CH$_2$.
3. The method of claim 1, wherein n is 5 or 6.
4. The method of claim 1, wherein said compound is selected from the group consisting of:
Compound 5 (AI01), 1-(4-(heptyloxy)phenyl)-3-(4-methylpiperazin-1-yl)propan-1-one,
Compound 6 (MD63), 3-morpholino-1-(4-(pentylthio)phenyl)propan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 12 (FT013), 3-(4-methylpiperazin-1-yl)-1-(4-(pentylthio)phenyl)propan-1-one, Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 15 (GR376), 3-morpholino-1-(4-(pentylselenyl)phenyl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 21 (GR379), 3-(4-methylpiperazin-1-yl)-1-(4-(pentylselenyl)phenyl)propan-1-one,
Compound 22 (GR383), 1-(4-(hexylselenyl)phenyl)-3-(4-methylpiperazin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
and
Compound 26 (GR392), 1-(4-heptylphenyl)-3-(4-methylpiperazin-1-yl)propan-1-one.

5. The method of claim 4, wherein said compound is selected from the group consisting of:
Compound 5 (AI01), 1-(4-(heptyloxy)phenyl)-3-(4-methylpiperazin-1-yl)propan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
and
Compound 26 (GR392), 1-(4-heptylphenyl)-3-(4-methylpiperazin-1-yl)propan-1-one.

6. The method of claim 5, wherein said compound is selected from the group consisting of:
Compound 8 (FT017), 1-(4-(heptylthio)phenyl)-3-morpholinopropan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 24 (GR390), 1-(4-heptylphenyl)-3-morpholinopropan-1-one,
Compound 26 (GR392), 1-(4-heptylphenyl)-3-(4-methylpiperazin-1-yl)propan-1-one.

7. A 1-phenylpropanone compound of formula (I)

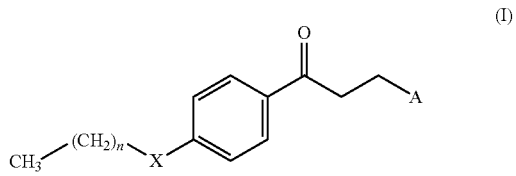

or a pharmaceutically acceptable salt thereof
wherein:
X is a methylene group (—$CH_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a ($C_1$-$C_3$)alkyl or ($C_1$-$C_3$)acyl radical,
with the proviso that
when X is O, A is 4-methyl-1-piperazinyl, and n is equal to 6,
when X is S and n is 5, then A is 4-methyl-1-piperazinyl,
when X is Se and A is 1-piperidinyl, then n is 6,
when X is $CH_2$, n is equal to 5, and A is 4-methyl-1-piperazinyl or 4-morpholyl.

8. The compound of claim 7, wherein X is selected from the group consisting of S, Se or $CH_2$.

9. The compound of claim 7, wherein n is 5 or 6.

10. The compound of claim 8, wherein said compound is selected from the group consisting of:
Compound 5 (AI01), 1-(4-(heptyloxy)phenyl)-3-(4-methylpiperazin-1-yl)propan-1-one,
Compound 6 (MD63), 3-morpholino-1-(4-(pentylthio)phenyl)propan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 12 (FT013), 3-(4-methylpiperazin-1-yl)-1-(4-(pentylthio)phenyl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 15 (GR376), 3-morpholino-1-(4-(pentylselenyl)phenyl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 21 (GR379), 3-(4-methylpiperazin-1-yl)-1-(4-(pentylselenyl)phenyl)propan-1-one,
Compound 22 (GR383), 1-(4-(hexylselenyl)phenyl)-3-(4-methylpiperazin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one, and
Compound 26 (GR392), 1-(4-heptylphenyl)-3-(4-methylpiperazin-1-yl)propan-1-one.

11. The compound of claim 10, wherein said compound is selected from the group consisting of:
Compound 5 (AI01), 1-(4-(heptyloxy)phenyl)-3-(4-methylpiperazin-1-yl)propan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one, and
Compound 26 (GR392), 1-(4-heptylphenyl)-3-(4-methylpiperazin-1-yl)propan-1-one.

12. The compound of claim 11, wherein said compound is selected from the group consisting of:
Compound 8 (FT017), 1-(4-(heptylthio)phenyl)-3-morpholinopropan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 24 (GR390), 1-(4-heptylphenyl)-3-morpholinopropan-1-one, and
Compound 26 (GR392), 1-(4-heptylphenyl)-3-(4-methylpiperazin-1-yl)propan-1-one.

13. A pharmaceutical composition comprising a compound of formula (I)

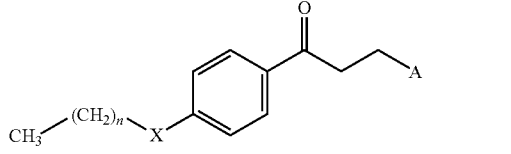

or a pharmaceutically acceptable salt thereof
wherein:
X is a methylene group (—CH$_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a ($C_1$-$C_3$)alkyl or ($C_1$-$C_3$)acyl radical,
with the proviso that
when X is O, A is 4-methyl-1-piperazinyl, and n is equal to 6,
when X is S and n is 5, then A is 4-methyl-1-piperazinyl or 4-morpholyl,
when X is Se and A is 1-piperidinyl, then n is 6,
when X is CH$_2$, n is equal to 5, and A is 4-methyl-1-piperazinyl or 4-morpholyl; and a pharmaceutically acceptable vehicle.

14. The pharmaceutical composition of claim 13, wherein said compound is selected from the group consisting of:
Compound 5 (AI01), 1-(4-(heptyloxy)phenyl)-3-(4-methylpiperazin-1-yl)propan-1-one,
Compound 6 (MD63), 3-morpholino-1-(4-(pentylthio)phenyl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 12 (FT013), 3-(4-methylpiperazin-1-yl)-1-(4-(pentylthio)phenyl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 15 (GR376), 3-morpholino-1-(4-(pentylselenyl)phenyl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 21 (GR379), 3-(4-methylpiperazin-1-yl)-1-(4-(pentylselenyl)phenyl)propan-1-one,
Compound 22 (GR383), 1-(4-(hexylselenyl)phenyl)-3-(4-methylpiperazin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one, and
Compound 26 (GR392), 1-(4-heptylphenyl)-3-(4-methylpiperazin-1-yl)propan-1-one.

15. The pharmaceutical composition of claim 14, wherein said compound is selected from the group consisting of:
Compound 5 (AI01), 1-(4-(heptyloxy)phenyl)-3-(4-methylpiperazin-1-yl)propan-1-one,
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one, and Compound 26 (GR392), 1-(4-heptylphenyl)-3-(4-methylpiperazin-1-yl)propan-1-one.

16. The pharmaceutical composition of claim 15, wherein said compound is selected from the group consisting of:
Compound 7 (VP158), 1-(4-(hexylthio)phenyl)-3-morpholinopropan-1-one,
Compound 8 (FT017), 1-(4-(heptylthio)phenyl)-3-morpholinopropan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 24 (GR390), 1-(4-heptylphenyl)-3-morpholinopropan-1-one, and
Compound 26 (GR392), 1-(4-heptylphenyl)-3-(4-methylpiperazin-1-yl)propan-1-one.

17. A method for treating a tumor comprising the step of administering a compound of formula (I)

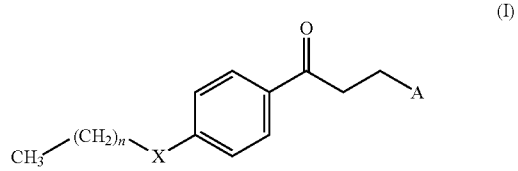

(I)

or a pharmaceutically acceptable salt thereof
wherein:
X is a methylene group (—CH$_2$—) or an atom selected from the group consisting of O, S and Se,
n is an integer from 4 to 6,
A is a substituent selected from the group consisting of 4-morpholyl, 1-piperidinyl and 4-methyl-1-piperazinyl, and it is optionally substituted with a (C$_1$-C$_3$)alkyl or (C$_1$-C$_3$)acyl radical,
with the proviso that
when X is O, A is 4-methyl-1-piperazinyl, and n is equal to 6,
when X is S and n is 5, then A is 4-methyl-1-piperazinyl,
when X is Se and A is 1-piperidinyl, then n is 6,
when X is CH$_2$, n is equal to 5, and A is 4-methyl-1-piperazinyl or 4-morpholyl.

18. The method of claim 17, wherein the tumor is breast cancer, hepatocarcinoma, chronic lymphatic leukemia or neuroblastoma.

19. The method of claim 17, wherein X is selected from the group consisting of S, Se or CH$_2$.

20. The method of claim 17, wherein n is 5 or 6.

21. The method of claim 17, wherein the 1-phenylpropanone compound is selected from the group consisting of:
Compound 5 (AI01), 1-(4-(heptyloxy)phenyl)-3-(4-methylpiperazin-1-yl)propan-1-one,
Compound 6 (MD63), 3-morpholino-1-(4-(pentylthio)phenyl)propan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 12 (FT013), 3-(4-methylpiperazin-1-yl)-1-(4-(pentylthio)phenyl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 15 (GR376), 3-morpholino-1-(4-(pentylselenyl)phenyl)propan-1-one,
Compound 16 (GR377), 1-(4-(hexylselenyl)phenyl)-3-morpholinopropan-1-one,
Compound 17 (GR386), 1-(4-(heptylselenyl)phenyl)-3-morpholinopropan-1-one, ene;
Compound 20 (GR387), 1-(4-(heptylselenyl)phenyl)-3-(piperidin-1-yl)propan-1-one,
Compound 21 (GR379), 3-(4-methylpiperazin-1-yl)-1-(4-(pentylselenyl)phenyl)propan-1-one,
Compound 22 (GR383), 1-(4-(hexylselenyl)phenyl)-3-(4-methylpiperazin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
and
Compound 26 (GR392), 1-(4-heptylphenyl)-3-(4-methylpiperazin-1-yl)propan-1-one.

22. The method of claim 21, wherein said compound is selected from the group consisting of:
Compound 5 (AI01), 1-(4-(heptyloxy)phenyl)-3-(4-methylpiperazin-1-yl)propan-1-one,
Compound 8 (FT017), 1-(4-(heptylthio)phenyl)-3-morpholinopropan-1-one,
Compound 9 (MC12), 1-(4-(pentylthio)phenyl)-3-(piperidin-1-yl)propan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 20 (GR387), 1-(4-(heptylselenyl)phenyl)-3-(piperidin-1-yl)propan-1-one,
Compound 23 (GR388), 1-(4-(heptylselenyl)phenyl)-3-(4-methylpiperazin-1-yl)propan-1-one,
Compound 24 (GR390), 1-(4-heptylphenyl)-3-morpholinopropan-1-one,
and
Compound 26 (GR392), 1-(4-heptylphenyl)-3-(4-methylpiperazin-1-yl)propan-1-one.

23. The method of claim 22, wherein said compound is selected from the group consisting of:
Compound 8 (FT017), 1-(4-(heptylthio)phenyl)-3-morpholinopropan-1-one,
Compound 11 (FT018), 1-(4-(heptylthio)phenyl)-3-(piperidin-1-yl)propan-1-one,
Compound 13 (FT016), 1-(4-(hexylthio)phenyl)-3-(4-methylpiperazin-1-yl)propan-1-one,
Compound 14 (FT019), 1-(4-(heptylthio)phenyl)-3-(4-methylpiperazin-1-yl)propan-1-one,
Compound 17 (GR386), 1-(4-(heptylselenyl)phenyl)-3-morpholinopropan-1-one,
Compound 24 (GR390), 1-(4-heptylphenyl)-3-morpholinopropan-1-one,
Compound 26 (GR392), 1-(4-heptylphenyl)-3-(4-methylpiperazin-1-yl)propan-1-one.

24. The compound of claim 8, wherein X is S.
25. The method of claim 2, wherein X is S.
26. The method of claim 17, wherein X is S.

* * * * *